(12) United States Patent
Theriot

(10) Patent No.: US 12,419,767 B1
(45) Date of Patent: Sep. 23, 2025

(54) KNEE BRACE APPARATUS

(71) Applicant: ManaMed, LLC, Denton, TX (US)

(72) Inventor: Trevor Theriot, Denton, TX (US)

(73) Assignee: ManaMed, LLC, Denton, TX (US)

( * ) Notice: Subject to any disclaimer, the term of this patent is extended or adjusted under 35 U.S.C. 154(b) by 42 days.

(21) Appl. No.: 18/664,755

(22) Filed: May 15, 2024

Related U.S. Application Data

(60) Provisional application No. 63/466,384, filed on May 15, 2023.

(51) Int. Cl.
*A61F 5/01* (2006.01)

(52) U.S. Cl.
CPC .... *A61F 5/0123* (2013.01); *A61F 2005/0167* (2013.01)

(58) Field of Classification Search
CPC ................ A61H 1/0255; A61H 1/0262; A61H 2001/0251; A61H 1/0237; A61F 5/0106; A61F 5/0123; A61F 5/0585; A61F 5/0102; A61F 2005/0132; A61F 2005/0167; A61F 5/0125
See application file for complete search history.

(56) References Cited

U.S. PATENT DOCUMENTS

| | | | |
|---|---|---|---|
| 5,823,931 A | 10/1998 | Gilmour | |
| 7,758,527 B2 | 7/2010 | Gilmour et al. | |
| 8,070,703 B2 | 12/2011 | Skahan et al. | |
| 8,454,543 B2 | 6/2013 | Skahan et al. | |
| 8,936,560 B2 * | 1/2015 | Lunau | A61F 5/0123 602/2 |
| 9,198,792 B2 | 12/2015 | Skahan et al. | |
| 9,327,119 B2 | 5/2016 | Skahan et al. | |
| D787,076 S | 5/2017 | Siddiqui et al. | |
| D849,253 S | 5/2019 | Siddiqui et al. | |
| 10,369,037 B2 | 8/2019 | Siddiqui et al. | |
| D898,204 S | 10/2020 | Siddiqui et al. | |
| D946,770 S | 3/2022 | Theriot | |

OTHER PUBLICATIONS

OActive® 2 Osteoarthritis Knee Bracing—VQ OrthoCare Wholesale Division. https://www.vqorthocare.com/product/oactive-2-osteoarthritis-knee-bracing/.

* cited by examiner

*Primary Examiner* — Ophelia A Hawthorne
(74) *Attorney, Agent, or Firm* — Holland & Knight LLP; Matthew C. Cox; Forrest S. Tinnin

(57) ABSTRACT

The present disclosure provides a knee brace apparatus and methods. The knee brace apparatus may include a sleeve, a hinge, a first strut, a second strut, a pin, a cross-bar, a manual adjustment tab, and a tool fitting. The first and second struts may be disposed on the hinge and the sleeve. The first and second struts may be configured to pivot about mediolateral axes. The first strut may include a joint. The joint may be configured to pivot a portion of the first strut about an anteroposterior axis. The pin may be disposed on the joint and be configured to operate the pivoting of the first strut. The cross-bar may be disposed on the pin, the manual adjustment tab may be disposed on the cross-bar, and the tool fitting may be disposed on the pin.

20 Claims, 39 Drawing Sheets

KNEE BRACE APPARATUS

CROSS-REFERENCES TO RELATED APPLICATIONS

This application is a non-provisional of and claims priority to U.S. Provisional Application No. 63/466,384, filed May 15, 2023, entitled KNEE BRACE APPARATUS, which is hereby incorporated by reference in its entirety.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO SEQUENCE LISTING OR COMPUTER PROGRAM LISTING INDEX

Not applicable.

BACKGROUND

The present invention relates generally to treating osteoarthritis, and more particularly to knee brace apparatuses for treating knee arthritis.

Osteoarthritis, particularly knee arthritis, is caused by cartilage in a knee deteriorating over time. Such deterioration may occur due to physical strain or age. Osteoarthritis may result in swelling of the knee, chronic pain, and a lack of mobility in the knee. Many conventional systems for treating knee arthritis includes applying a knee brace to a leg of a patient. Knee braces typically increase knee mobility and reduce pain caused from knee arthritis. Such therapy may be provided in terms of providing a secure embrace around the knee to reduce swelling, enforcing a proper knee bending movement, or applying a pressure or adjustment to the knee that corrects the internal issues causing physical strain in the knee. However, conventional knee braces present a number of issues.

As a first example, many conventional knee braces may be configured to apply a varus (e.g., "bow-legged") or valgus (e.g., "buckled") pressure or adjustment to the knee, thereby reducing physical strain that may be caused by bone-on-bone contact within the knee. Problematically, such varus or valgus configurations in conventional knee braces are typically cumbersome to operate. For instance, the components facilitating varus or valgus configurations may be fixed when the knee brace is provided to the patient, and thus the patient must either replace the knee brace or return to a providing caregiver in order for the knee brace to be adjusted. Moreover, in cases where the varus or valgus configurations of the knee brace are independently adjustable by the patient, such components typically require additional tools or precise handling of the knee brace components. In such cases, the patient may either lose the tool, need to take the knee brace off in order to adjust the knee brace, or simply be discouraged from adjusting the knee brace at all.

As another example, conventional knee braces typically include fasteners or straps configured to secure the knee brace to the user. Such fasteners or straps typically join one end of the knee brace to another end of the knee brace, such that the knee brace is wrapped around the leg of the user. Problematically, such fasteners or straps may not provide an optimally secure embrace of the leg, and therefore do not provide as much reduction in swelling of the knee as possible, among other issues.

It would be advantageous to provide a knee brace that is more easily adjustable in terms of varus and/or valgus pressure or adjustment, as well as a knee brace that provides a more secure embrace around the leg.

What is needed, therefore, are improved apparatuses and methods for the treatment of osteoarthritis, particularly, knee arthritis, via knee brace apparatuses.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The present disclosure provides a knee brace apparatus, which may be operable to treat knee arthritis. In some embodiments, the knee brace apparatus be operable to apply a varus or valgus pressure or adjustment to a knee of a leg. The knee brace apparatus may include a hinge, a first strut, a second strut, a first pin, a first cross-bar, a first manual adjustment tab, and a first tool fitting.

The first strut may include a proximal portion disposed on the hinge, a distal portion configured to be secured to a thigh of the leg, and a first joint connecting the proximal portion of the first strut to the distal portion of the first strut, such that the distal portion of the first strut is configured to pivot about a first anteroposterior axis defined by the first joint. The first strut may be configured to pivot about a first mediolateral axis with respect to the hinge. The second strut may include a proximal portion disposed on the hinge and a distal portion configured to be secured to a calf of the leg. The second strut may be configured to pivot about a second mediolateral axis with respect to the hinge. The first pin may be disposed on the distal portion of the first strut and mechanically engaged with the first joint. The first pin may be configured to be rotated relative to the first joint. The first cross-bar may be disposed on the first pin. The first manual adjustment tab may be disposed on the first cross-bar, configured to be pivoted about the first cross-bar, and configured to be rotated relative to the first joint. The first tool fitting may be disposed on the first pin. When the first manual adjustment tab is rotated relative to the first joint, the first pin may be rotated relative to the first joint, such that the mechanical engagement between the first pin and the first joint effectuates pivoting the distal portion of the first strut about the first anteroposterior axis.

In some embodiments of the present disclosure, the first tool fitting is a first key-hole extending into a top surface of a distal portion of the first pin, such that a tool may be inserted into the first key-hole in order to rotate the first pin relative to the first joint. In other embodiments of the present disclosure, the first tool fitting is a first turn-key projecting from the top surface of the distal portion of the first pin, such that the tool may grasp the first turn-key in order to rotate the first pin relative to the first joint. In even other embodiments of the present disclosure, the first tool fitting is a first recess extending into a side surface of the distal portion of the first pin, such that a tool may be inserted into the first recess in order to rotate the first pin relative to the first joint.

In some embodiments of the present disclosure, the second strut of the knee brace apparatus further includes a second joint connecting the proximal portion of the second strut to the distal portion of the second strut, such that the distal portion of the second strut is configured to pivot about a second anteroposterior axis defined by the second joint. In some embodiments, the knee brace apparatus further includes a second pin, a second cross-bar, a second manual adjustment tab, and a second tool fitting. The second pin may be disposed on the distal portion of the second strut and mechanically engaged with the second joint. The second pin may be configured to be rotated relative to the second joint. The second cross-bar may be disposed on the second pin. The second manual adjustment tab may be disposed on the second cross-bar, configured to be pivoted about the second cross-bar, and rotated relative to the second joint. When the second manual adjustment tab is rotated relative to the second joint, the second pin may be rotated relative to the second joint, such that the mechanical engagement between the second pin and the second joint effectuates pivoting the distal portion of the second strut about the second anteroposterior axis.

In some embodiments of the present disclosure, the second tool fitting is a second key-hole extending into a top surface of a distal portion of the second pin, such that a tool may be inserted into the second key-hole in order to rotate the second pin relative to the second joint. In other embodiments of the present disclosure, the second tool fitting is a second turn-key projecting from the top surface of the distal portion of the second pin, such that the tool may grasp the second turn-key in order to rotate the second pin relative to the second joint. In even other embodiments of the present disclosure, the second tool fitting is a second recess extending into a side surface of the distal portion of the second pin, such that a tool may be inserted into the second recess in order to rotate the second pin relative to the second joint.

Another aspect of the present disclosure is a knee brace apparatus. The knee brace apparatus may include the bracing apparatus and a sleeve including a first cuff and a second cuff. The distal portion of the first strut may be disposed on the first cuff of the sleeve, and the distal portion of the second strut may be disposed on the second cuff of the sleeve.

In some embodiments of the present disclosure, the knee brace apparatus further includes a first hook and a firs strap. The first strap may be disposed on the distal portion of the first strut. The first strap may be disposed on the first cuff of the sleeve. The first strap may be configured to be wrapped in a first direction around the sleeve, guided through the first hook, wrapped in a second direction opposite the first direction such that the first strap is secured to the first hook, and adhered to the first cuff. In some embodiments, when the first strap is wrapped in the first direction around the sleeve, the first strap is wrapped around the entirety of the sleeve.

In some embodiments of the present disclosure, the knee brace apparatus further includes a second hook and a second strap. The second strap may be disposed on the distal portion of the second strut. The second strap may be disposed on the second cuff of the sleeve. The second strap may be configured to be wrapped in a first direction around the sleeve, guided through the second hook, wrapped in a second direction opposite the first direction such that the second strap is secured to the second hook, and adhered to the second cuff. In some embodiments, when the second strap is wrapped in the first direction around the sleeve, the second strap is wrapped around the entirety of the sleeve.

Yet another aspect of the present disclosure is a knee brace method. The method may include providing the aforementioned knee brace apparatus. The method may further include securing the knee brace apparatus to the leg. The method may further include pivoting the first manual adjustment tab about the first cross-bar and rotating the first manual adjustment tab, such that the first pin is rotated relative to the first joint, and the mechanical engagement between the first pin and the first joint effectuates pivoting the distal portion of the first strut about the first anteroposterior axis. The method may further include pivoting the first strut about the first mediolateral axis with respect to the hinge. The method may further include pivoting the second strut about the second mediolateral axis with respect to the hinge. In some embodiments, the method further includes pivoting the second manual adjustment tab about the second cross-bar and rotating the second manual adjustment tab, such that the second pin is rotated relative to the second joint, and the mechanical engagement between the second pin and the second joint effectuates pivoting the distal portion of the second strut about the second anteroposterior axis. The method may further include engaging the first tool fitting with a tool, such that the first pin is rotated relative to the first joint, and the mechanical engagement between the first pin and the first joint effectuates pivoting the distal portion of the first strut about the first anteroposterior axis. The method may further include engaging the second tool fitting with the tool, such that the second pin is rotated relative to the second joint, and the mechanical engagement between the second pin and the second joint effectuates pivoting the distal portion of the second strut about the second anteroposterior axis.

Numerous other objects, advantages and features of the present disclosure will be readily apparent to those of skill in the art upon a review of the following drawings and description of a preferred embodiment.

DETAILED DESCRIPTION

Figure 1:
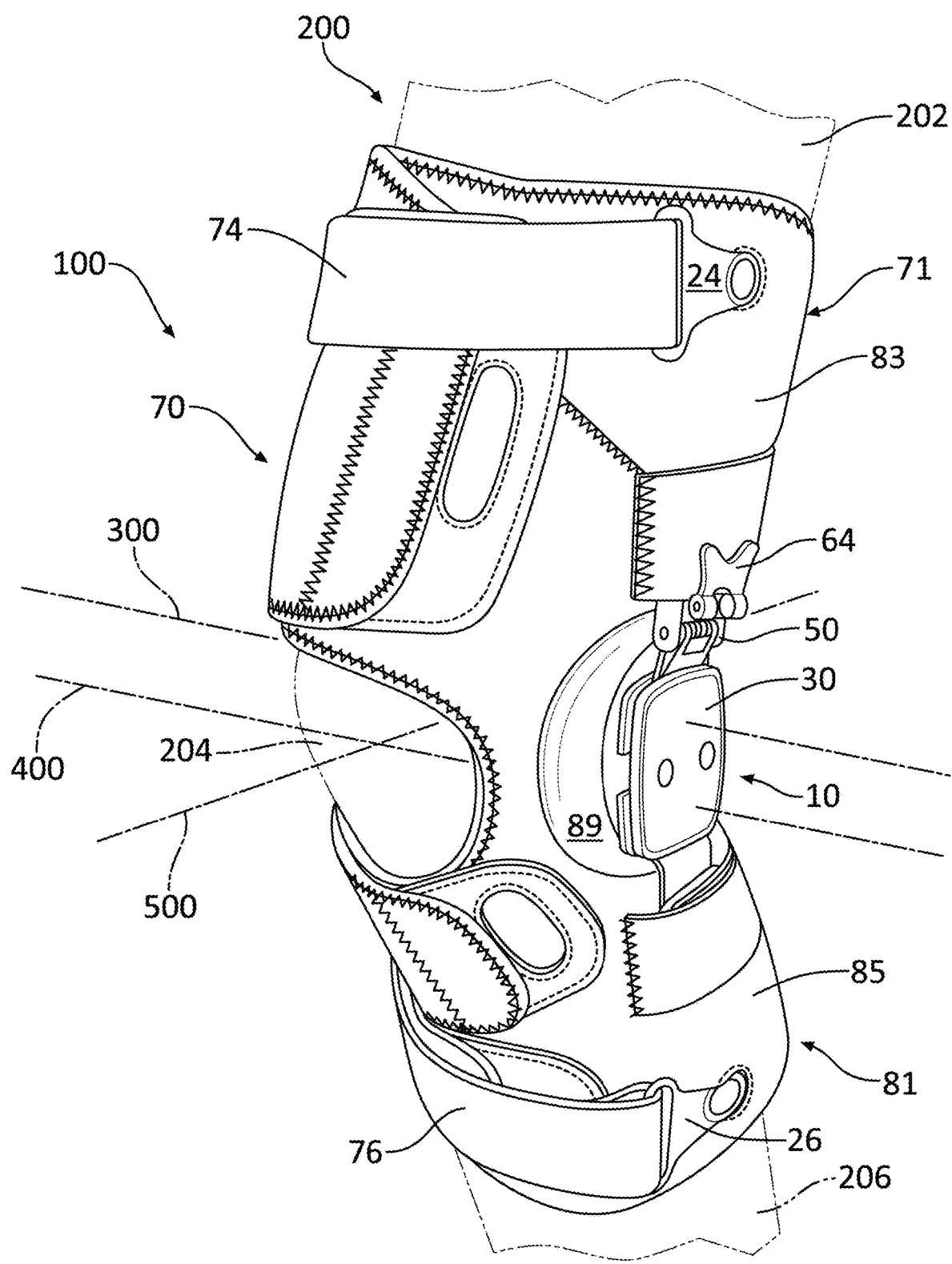
FIG. 1 is an isometric view of a user wearing a knee brace apparatus, according to some embodiments of the present disclosure.

While the making and using of various embodiments of the present disclosure are discussed in detail herein, it should be appreciated that the present disclosure provides many applicable inventive concepts that are embodied in a wide variety of specific contexts. The specific embodiments discussed herein are merely illustrative of specific ways to make and use the disclosure and do not delimit the scope of the disclosure. Those of ordinary skill in the art will recognize numerous equivalents to the specific apparatuses, systems, and methods described herein. Such equivalents are considered to be within the scope of this disclosure and may be covered by the claims.

Furthermore, the described features, structures, or characteristics of the disclosure may be combined in any suitable manner in one or more embodiments. In the description contained herein, numerous specific details are provided, such as examples of programming, software, user selections, hardware, hardware circuits, hardware chips, or the like, to provide understanding of embodiments of the disclosure. One skilled in the relevant art will recognize, however, that the disclosure may be practiced without one or more of the specific details, or with other methods, components, materials, apparatuses, devices, systems, and so forth. In other instances, well-known structures, materials, or operations may not be shown or described in detail to avoid obscuring aspects of the disclosure.

The aforementioned features and advantages of the embodiments will become more fully apparent from the description and appended claims, or may be learned by the practice of embodiments as set forth herein. As will be appreciated by one skilled in the art, aspects of the present disclosure may be embodied as an apparatus, system, method, computer program product, or the like. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module," or "system." Furthermore, aspects of the present disclosure may take the form of a computer program product embodied in one or more computer-readable media having program code embodied thereon.

In the drawings, not all reference numbers are included in each drawing, for the sake of clarity. In addition, positional terms such as "upper," "lower," "side," "top," "bottom," etc. refer to the apparatus when in the orientation shown in the drawing. A person of skill in the art will recognize that the apparatus can assume different orientations when in use.

The words "connected", "attached", "joined", "mounted", "fastened", and the like should be interpreted to mean any manner of joining two objects including, but not limited to, the use of any fasteners such as screws, nuts and bolts, bolts, pin and clevis, and the like allowing for a stationary, translatable, or pivotable relationship; welding of any kind such as traditional MIG welding, TIG welding, friction welding, brazing, soldering, ultrasonic welding, torch welding, inductive welding, and the like; using any resin, glue, epoxy, and the like; being integrally formed as a single part together; any mechanical fit such as a friction fit, interference fit, slidable fit, rotatable fit, pivotable fit, and the like; any combination thereof; and the like.

Referring now to FIG. 1, a knee brace assembly (assembly) 100 is shown, according to some embodiments of the present disclosure. The assembly 100 may be worn on a leg 200 of a user in order to treat osteoarthritis or, more particularly, knee arthritis occurring in a knee 204 of the leg 200. In some embodiments, the assembly 100 includes a knee bracing apparatus (apparatus) 10. The apparatus 10 may be secured to a sleeve 70, and thereby secured to the leg 200 by the sleeve 70. As discussed in greater detail below, the apparatus 10 may include various joints and hinges configured to facilitate movement and/or adjustment of the knee 204, thereby treating the knee 204 for arthritis. As generally depicted herein, the knee 204 is a left knee and, accordingly, the assembly 100 and the apparatus 10 are generally shown as configured for a left knee. However, it should be appreciated that the assemblies, apparatuses, and methods provided herein may be analogously applied to a right knee.

In some embodiments, the sleeve 70 is tubular-shaped, elastic, and flexible. For example, the sleeve 70 may be constructed of lightweight and cushioned neoprene fabric. The sleeve 70 may include a first (e.g., upper) cuff 71 which secures the sleeve 70 above the knee 204 (e.g., to a thigh 202 of the leg 200), as well as a second (e.g., lower) cuff 81 which secures the sleeve 70 below the knee 204 (e.g., to a calf or shin 206) of the leg 200. As described in greater detail below, the sleeve 70 may include various folds, straps, and other fasteners that secure the first cuff 71 to the thigh 202 and the second cuff 81 to the calf 206, thereby allowing the sleeve 70 to provide compression on the leg 200, which may allow for warmth and decreases in swelling associated with osteoarthritis. As shown, the first cuff 71 and the second cuff 81 may meet about the knee 204 of the leg 200 between the thigh 202 and the calf 206, where the sleeve 70 forms an opening for enveloping the knee 204. While generally referred to herein as a "sleeve," the sleeve 70 may alternatively be understood as a wrap, a compression sleeve, a compression wrap, and so on.

Figure 2:
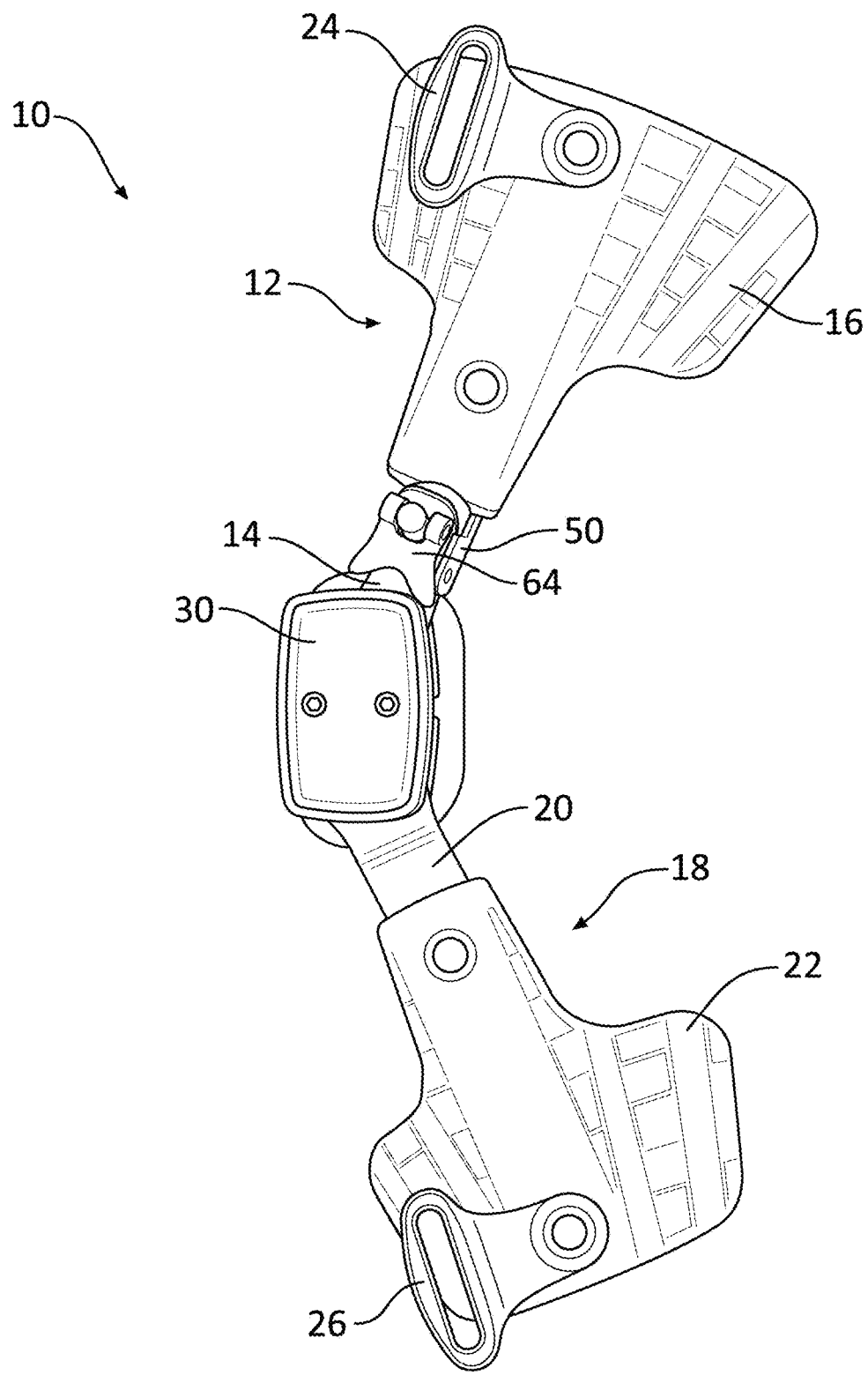
FIG. 2 is a front view of a brace apparatus for a knee brace apparatus, according to some embodiments of the present disclosure.

Referring now to FIG. 2, the apparatus 10 is shown, according to some embodiments of the present disclosure. In some embodiments, the apparatus 10 includes a first (e.g., upper) strut 12, a second (e.g., lower) strut 18, and a hinge 30 connecting the first strut 12 to the second strut 18. The first strut 12 may include a distal portion 16, as well as a proximal portion 14. Similarly, the second strut 18 may include a distal portion 22, as well as a proximal portion 20. The proximal portion 14 of the first strut 12, as well as the proximal portion 20 of the second strut 18, may each be disposed on, and be configured to rotate with respect to, the hinge 30. In this sense, the hinge 30 may connect the proximal portion 14 of the first strut 12 to the proximal portion 20 of the second strut 18.

The distal portion 16 of the first strut 12, as well as the distal portion 22 of the second strut 18, may be disposed on the sleeve 70 and secured to the leg 200 by the sleeve 70. As a first example, the distal portion 16 of the first strut 12 may be secured within a first (e.g., upper) pocket 83 (depicted with reference to FIG. 1) of the sleeve 70 disposed on the first cuff 71, and therefore be secured to the leg 200 above the knee 204 (e.g., to the thigh 202). As a second example, the distal portion 22 of the second strut 18 may be secured within a second (e.g., lower) pocket 85 (depicted with reference to FIG. 1) of the sleeve 70 disposed on the second cuff 81, and therefore be secured to the leg 200 below the knee 204 (e.g., to the calf or shin 206).

As shown, the distal portion 16 of the first strut 12 and the distal portion 22 of the second strut 22 may expand, relative to the respective proximal portions 14, 20 into fans. Such fans may be contoured in order to account for the shape of the thigh 202 or the calf 206 (thereby providing a secure fit to the leg 200), as well as to provide a substantial surface for being secured within the first and second pockets 83, 85. The hinge 30 may be adhered (e.g., via Velcro) to the sleeve 70 in between the first and second cuffs 52, 54.

Due to the aforementioned engagement between the first strut 12 and the first pocket 83, the aforementioned engagement between the second strut 18 and the second pocket 85, and the aforementioned adherence of the hinge 30 to the sleeve 70 between the first cuff 71 and the second cuff 81, the, the apparatus 10 may accordingly be secured to the sleeve 70, and therefore the leg 200. As described in greater detail below with reference to FIG. 3, the first strut 12 and the second strut 18 may be configured to pivot with respect to the hinge 30 (and therefore each other), such that the assembly 100 is configured to bend in a manner that mimics a physiological bending of the knee 204. For example, the hinge 30 may be configured to facilitate pivoting of the first strut 12 (and therefore the first cuff 71) about a first mediolateral axis 300 (depicted with reference to FIG. 1), as well as pivoting of the second strut 18 (and therefore the second cuff 81) about a second mediolateral axis 400 (depicted with reference to FIG. 1) parallel to the first mediolateral axis 300.

In some embodiments, the apparatus 10 includes a first joint 50 disposed on the first strut 12, allowing at least a portion of the first strut 12 to pivot about a first anteroposterior axis 500 (depicted with reference to FIG. 1) defined by an anteroposterior pivot point 52 (depicted with reference to FIG. 6) on the first joint 50. For example, as described in greater detail below with reference to FIGS. 6-8, the distal portion 16 of the first strut 12 may be pivoted about the anteroposterior pivot point 52 while the proximal portion 14 remains in a constant orientation (in terms of rotation about the first anteroposterior axis 500) with respect to the anteroposterior pivot point 52, and thus the hinge 30.

As described in greater detail below with reference to FIGS. 7-8, the hinge 30 and the second strut 18 may substantially retain their positions relative to the sleeve 70 and therefore the leg 200, and thus when the distal portion 16 of the first strut 12 is pivoted about the first mediolateral axis 500 as described herein, the apparatus 10 may thus apply a varus (e.g., "bow-legged") or a valgus (e.g., "buckling") pressure or adjustment to the knee 204. In some embodiments, the sleeve 70 includes a cushion 89 (depicted with reference to FIG. 1) located between the first and second cuffs 71, 81 in order to provide a more comfortable engagement between the hinge 30 (and the apparatus 10 in its entirety) and the leg 200. For example, the cushion 89 may be disposed on the sleeve 70, and the hinge 30 may be adhered to the cushion 89.

As mentioned above, the sleeve 70 may include various folds, straps, and other fasteners that secure the first cuff 71 of the sleeve 70 to the thigh 202 and the second cuff 81 of the sleeve 70 to the calf 206. In order to secure the assembly 100 to the leg 200 as such, some of the aforementioned straps may be secured to a first (e.g., upper) hook 24 disposed on the distal portion 16 of the first strut 12, as well as a second (e.g., lower) hook 26 disposed on the distal portion 22 of the second strut 18. As a first example, and as depicted with reference to FIG. 1, the first cuff 71 may include a first opening allowing the first hook 24 to extend out of the first pocket 83 (and therefore free of the sleeve 70) in order to retain a first (e.g., upper) strap 74. As a second example, and as depicted with reference to FIG. 1, the second cuff 81 may include a second opening allowing the second hook 26 to extend out of the second pocket 85 (and therefore free of the sleeve 70) in order to retain a second (e.g., lower) strap 76. The first and second hooks 24, 26 may be pivotally secured to the first and second struts 12, 18 in order to facilitate such engagement with the first and second straps 74, 76 (respectively).

Figure 6:
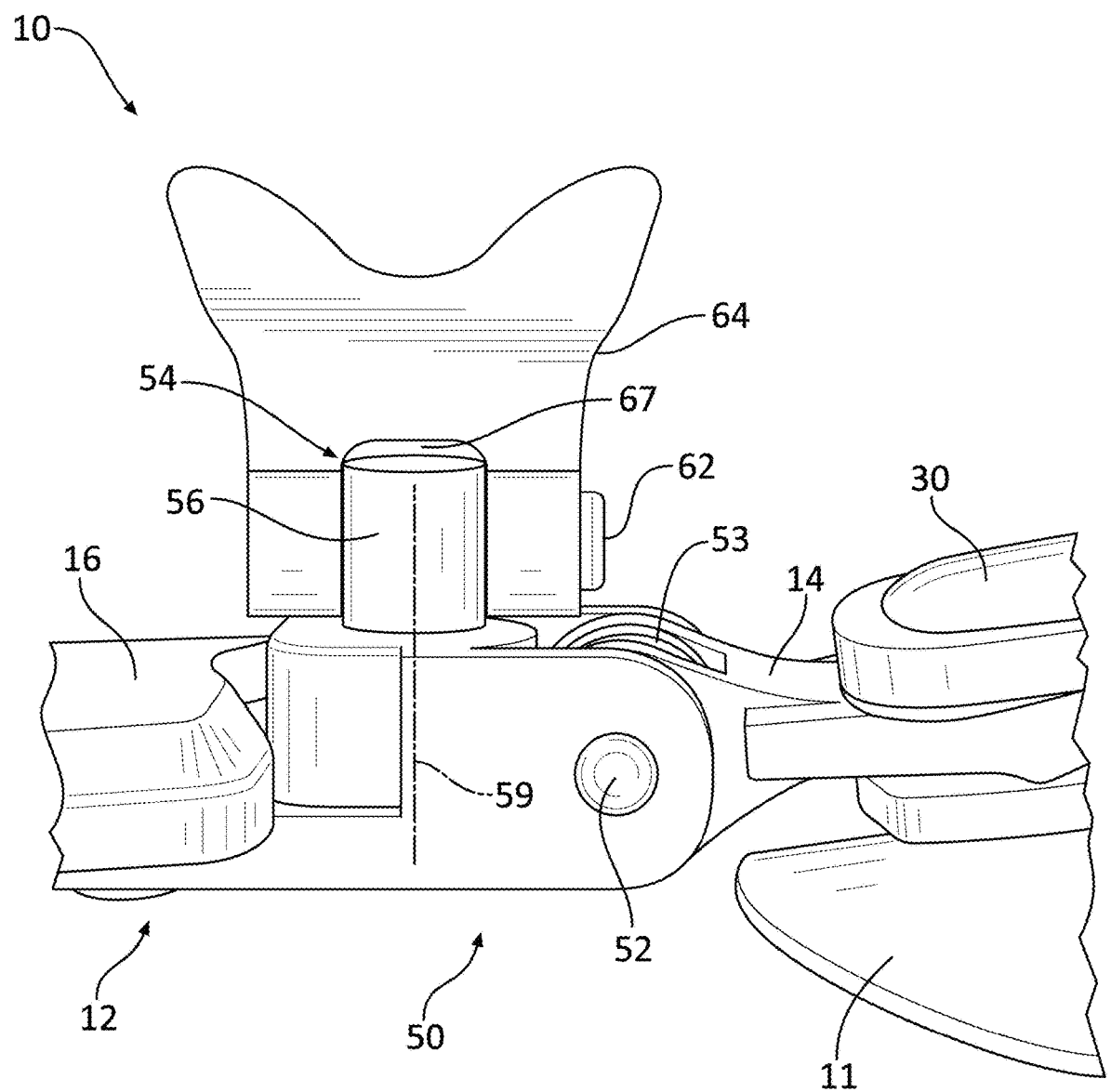
FIG. 6 is a detailed side perspective view of a joint for a knee brace apparatus, according to some embodiments of the present disclosure.
Figure 7:
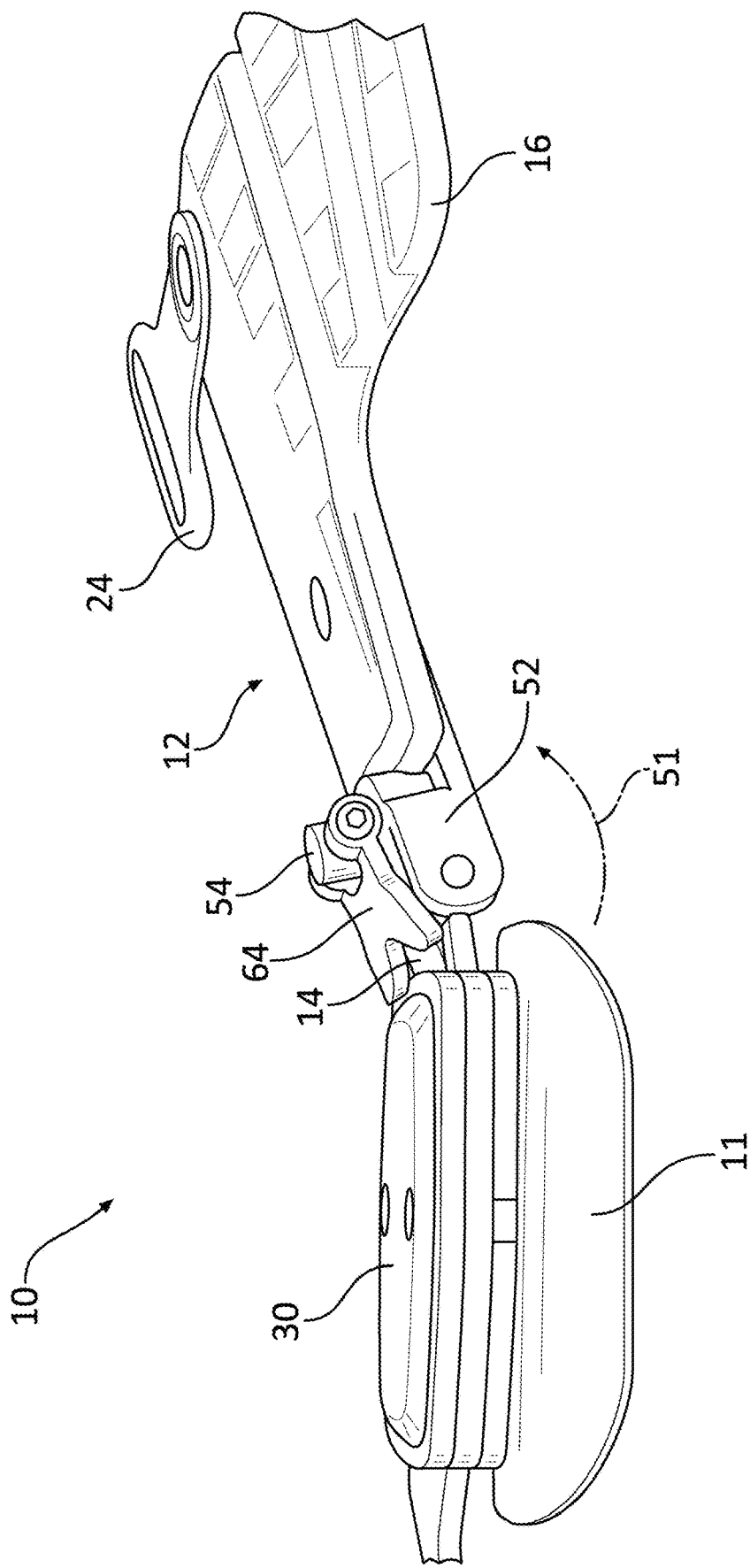
FIG. 7 is a side perspective view of a joint for a knee brace apparatus performing a pivot, according to some embodiments of the present disclosure.
Figure 8:
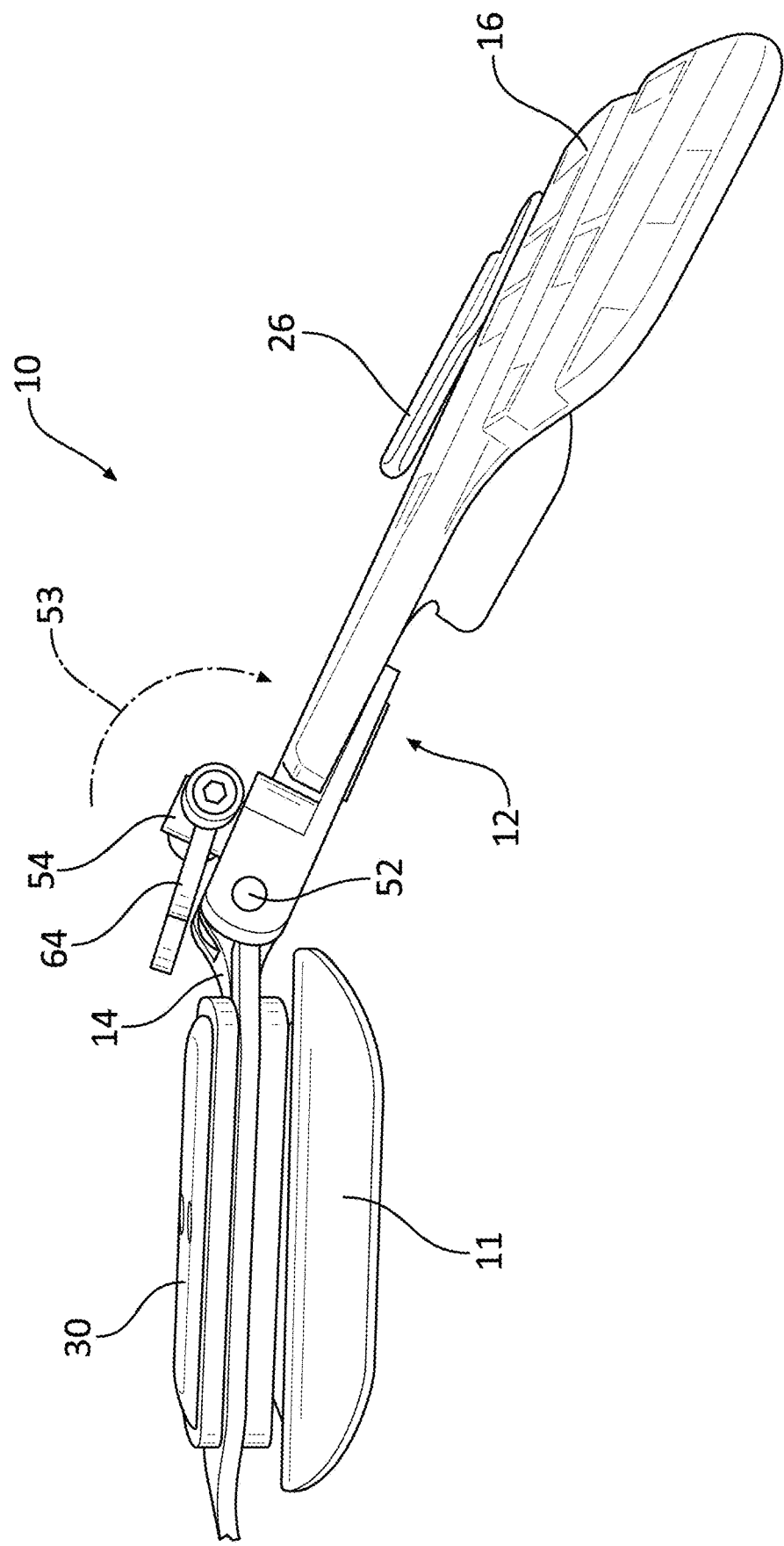
FIG. 8 is a side perspective view of a joint for a knee brace apparatus forming a pivot, according to some embodiments of the present disclosure.

In some embodiments, the apparatus 10 includes a base 11, as shown with reference to FIGS. 6-8. The base 11 may be a curved member configured to facilitate adhering the hinge 30 to the sleeve 70 (or the cushion 89 disposed thereon, in some cases).

Figure 3:
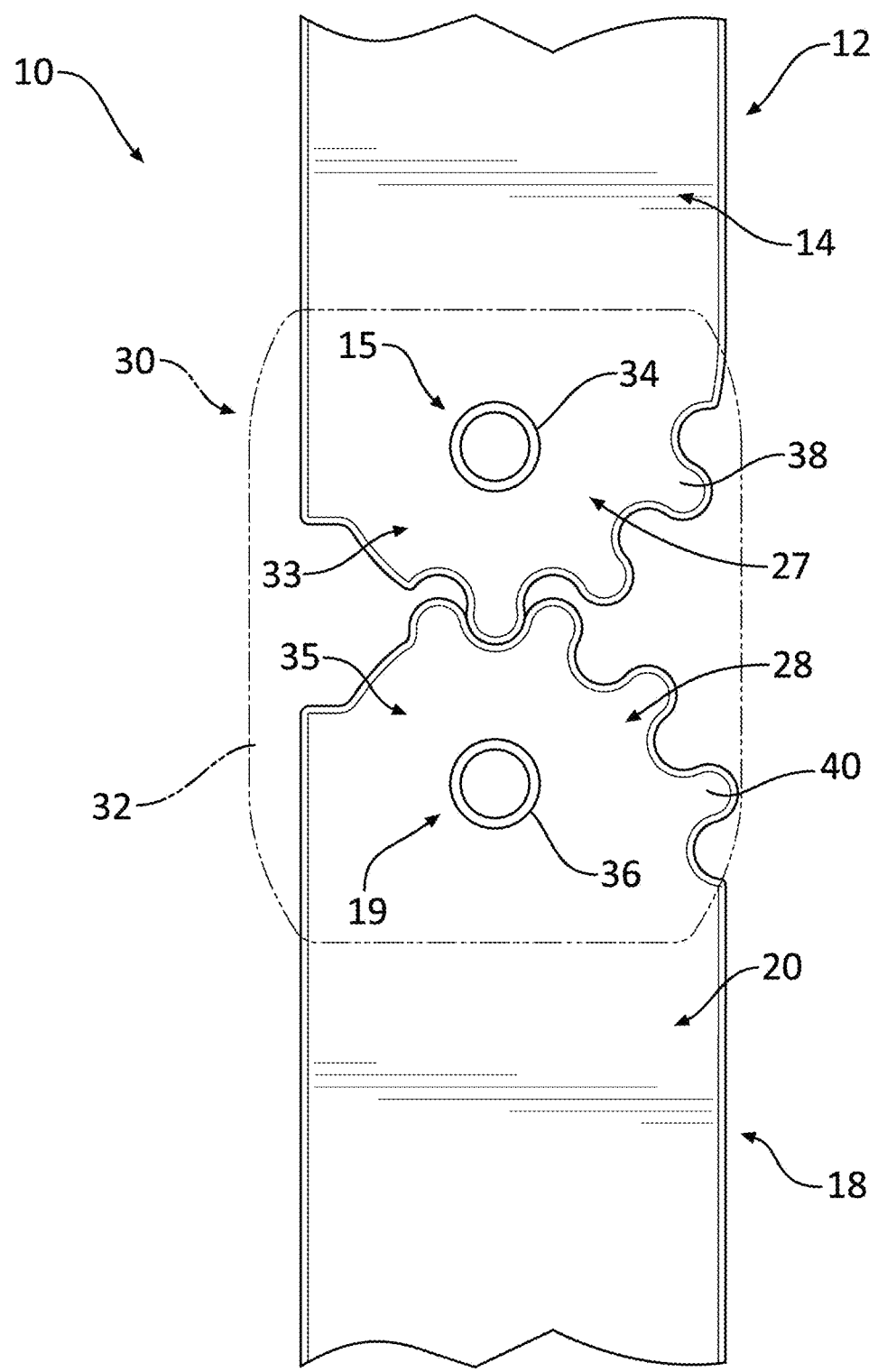
FIG. 3 is a front schematic view of a hinge for a knee brace apparatus, according to some embodiments of the present disclosure.
Figure 4:
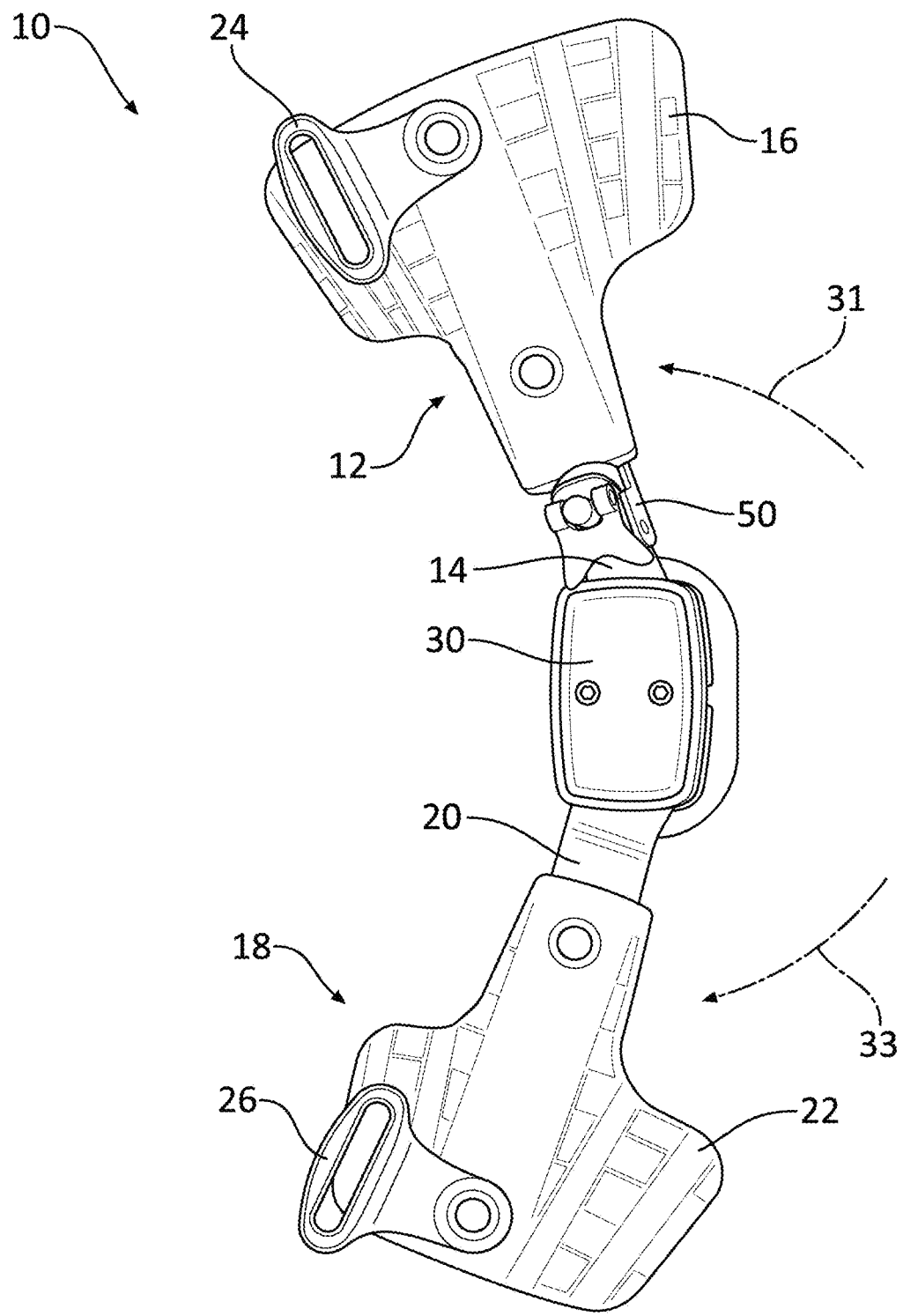
FIG. 4 is a front perspective view of a brace apparatus for a knee brace apparatus forming a bend, according to some embodiments of the present disclosure.
Figure 5:
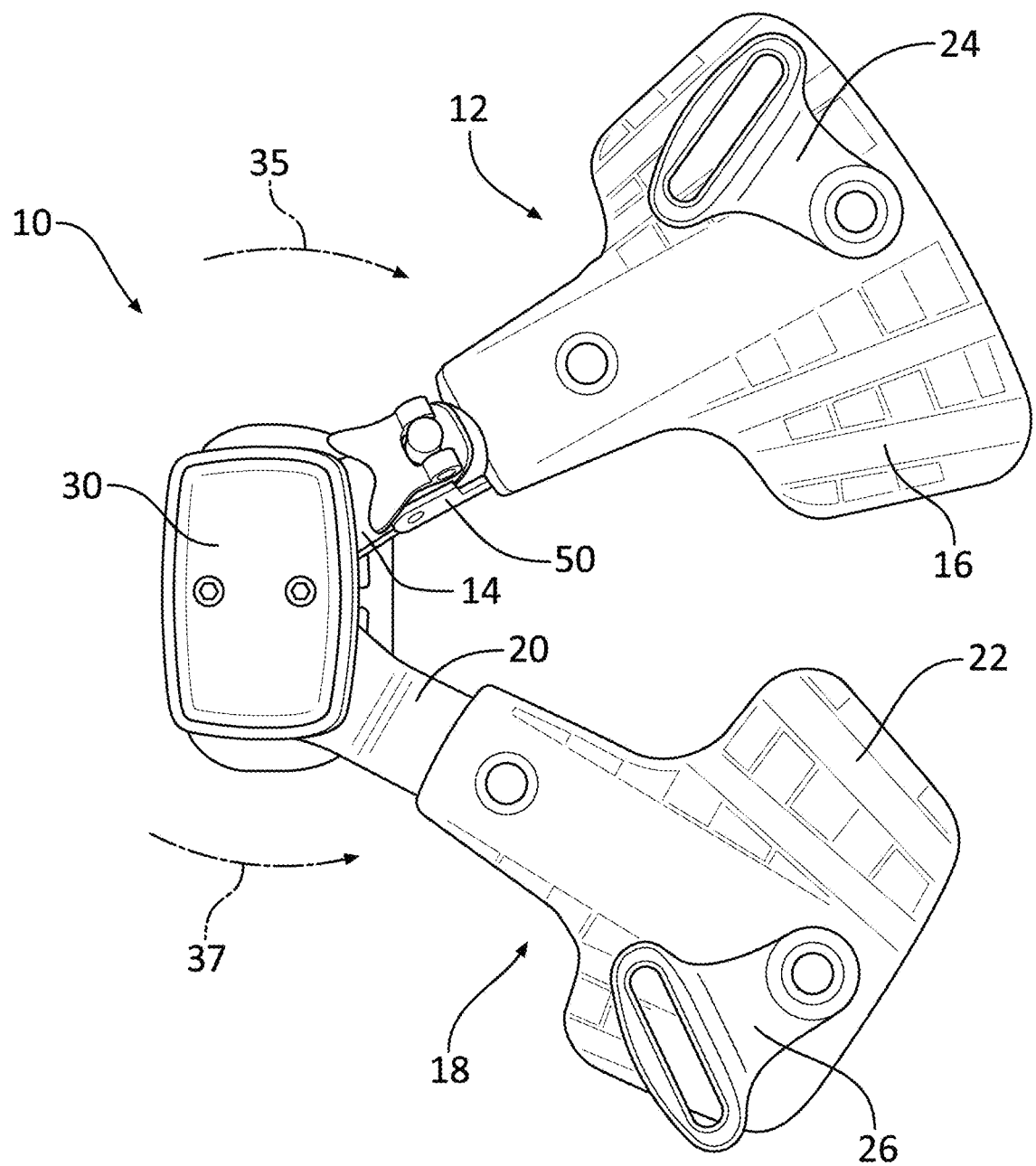
FIG. 5 is a front perspective view of a brace apparatus for a knee brace apparatus forming a bend, according to some embodiments of the present disclosure.

Referring now to FIGS. 3-5, the hinge 30 is shown in greater detail, according to some embodiments of the present disclosure. As mentioned above, the hinge 30 may be configured to facilitate pivoting of the first strut 12 about the first mediolateral axis 300 (depicted with reference to FIG. 1), as well as pivoting of the second strut 18 about the second mediolateral axis 400 (depicted with reference to FIG. 1) parallel to the first mediolateral axis 300, such that the assembly 100 is configured to bend in a manner that mimics a physiological bending of the knee 204.

The hinge 30 may include a hinge body (e.g., housing) 32. In some embodiments, a first (e.g., upper) mediolateral pivot point 15 on the proximal portion 14 of the first strut 12 may be rotatably coupled to the hinge body 32 at a corresponding upper pivot point 34 (the location of the first mediolateral axis 300) on the hinge body 32. Similarly, a second (e.g., lower) mediolateral pivot point 19 on the proximal portion 20 of the second strut 18 may be rotatably coupled to the hinge body 32 at a corresponding lower pivot point 36 (the location of the second mediolateral axis 400) on the hinge body 32.

In some embodiments, the proximal portion 14 of the first strut 12 includes a first number of teeth (e.g., first teeth, upper teeth) 38 circumferentially disposed about the first mediolateral pivot point 15 on the proximal portion 14 of the first strut 12. Similarly, the proximal portion 20 of the second strut 12 may include a second number of teeth (e.g., second teeth, lower teeth) 40 circumferentially disposed about the second mediolateral pivot point 19 on the proximal portion 20 of the second strut 18. The upper and lower pivot points 34, 46 on the hinge body 32 (and, therefore, the first and second mediolateral pivot points 15, 19 on the first and second struts 12, 18, respectively) may be located such that the first teeth 38 on the proximal portion 14 of the first strut 12 are mechanically engaged (e.g., meshed) with the second teeth 40 on the proximal portion 20 of the second strut 18. Accordingly, the first and second struts 12, 18 may be configured to pivot at a corresponding rate, thereby facilitating bending of the assembly 100 that is analogous to physiological bending of the knee 204, while simultaneously allowing varus or valgus pressure or adjustment to be applied to the knee 204 (via the first joint 50). As a first example, and as shown with reference to FIG. 4, the first and second struts 12, 18 may be configured to simultaneously pivot forward (e.g., in the same direction that the knee 204 is facing as depicted with reference to FIG. 1) along curvatures 31, 33 (respectively). As a second example, and as shown with reference to FIG. 5, the first and second struts 12, 18 may be configured to simultaneously pivot backward (in the opposite direction that the knee 204 is facing as depicted with reference to FIG. 1) along curvatures 35, 37 (respectively).

In some embodiments, the first teeth 38 are offset from the pivot point 34 of the hinge 30 such that more of the first teeth 38 are located on a rear portion 27 on the proximal portion 14 of the first strut 12 than a front portion 33 on the proximal portion 14 of the first strut 12. Similarly, the second teeth 40 may be offset from the pivot point 36 of the hinge 30 such that more of the second teeth 40 are located on a rear portion 28 on the proximal portion 20 of the second strut 18 than a front portion 35 of the proximal portion 20 of the second strut 18. In this sense, the knee 204 may be allowed to bend more towards the rear portions 27, 28 than the front portions 33, 35, thereby matching the physiological bending and/or locking of the knee 204 and preventing hyperextension of the knee 204. As a first example, and as shown with reference to FIG. 4, the first and second struts 12, 18 may be configured to simultaneously pivot forward along curvatures 31, 33 (respectively) until a maximum forward bend (as shown) is formed in the apparatus 10 (and thus the assembly 100). As a second example, and as shown with reference to FIG. 5, the first and second struts 12, 18 may be configured to simultaneously pivot backward along curvatures 35, 37 (respectively) until a maximum rearward bend (as shown) is formed in the apparatus 10 (and thus the assembly 100).

Referring now to FIGS. 6-8, the first joint 50 is shown in greater detail, according to some embodiments of the present disclosure. As mentioned above, the first joint 50 may be disposed on the first strut 12, connect the distal portion 16 of the first strut 12 to the proximal portion 14 of the first strut 12, and thereby allow the distal portion 16 of the first strut 12 to be pivoted about the anteroposterior pivot point 52 while the proximal portion 14 remains in a constant orientation with respect to the hinge 30. As a first example, and as depicted with reference to FIG. 7, the distal portion 16 of the first strut 12 may be pivoted about the anteroposterior pivot point 52 of the first joint 50 (and therefore the first anteroposterior axis 500 depicted with reference to FIG. 1) outward (e.g., away from the knee 204) along a curvature 51, thereby applying a varus pressure or readjustment to the knee 204. As a second example, and as depicted in FIG. 8, the distal portion 16 of the first strut 12 may be pivoted about the anteroposterior pivot point 52 of the first joint 50 (and therefore the first anteroposterior axis 500 depicted with reference to FIG. 1) inward (e.g., towards the knee 204) along a curvature 53, thereby applying a valgus pressure or readjustment to the knee 204. As discussed in greater detail below, the aforementioned pivoting of the distal portion 16 of the first strut 12 may be imparted or controlled by articulation of a first pin 54 mechanically engaged with component(s) of the first joint 50.

Figure 9:
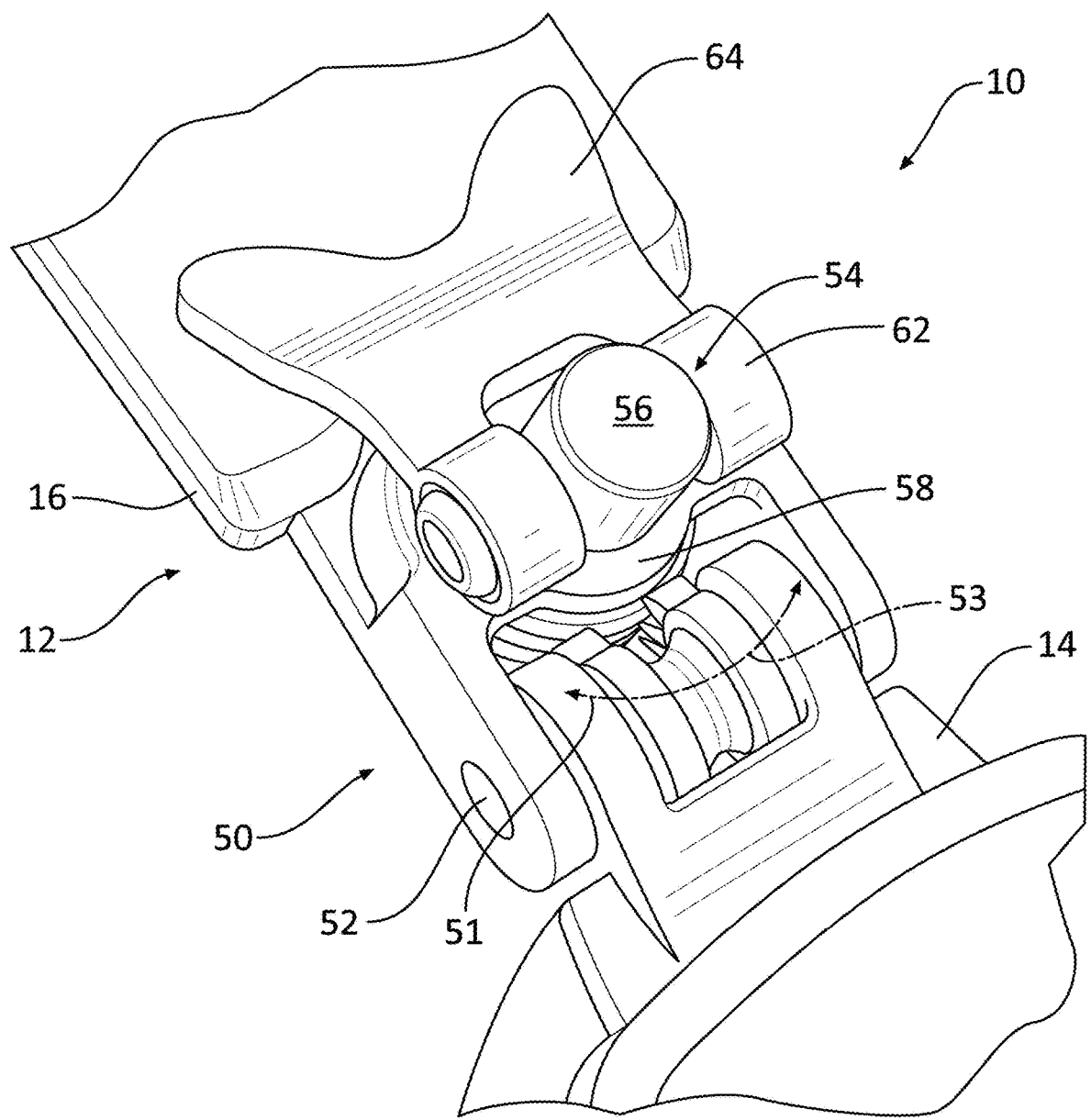
FIG. 9 is a detailed front perspective view of a joint for a knee brace apparatus, according to some embodiments of the present disclosure.
Figure 10:
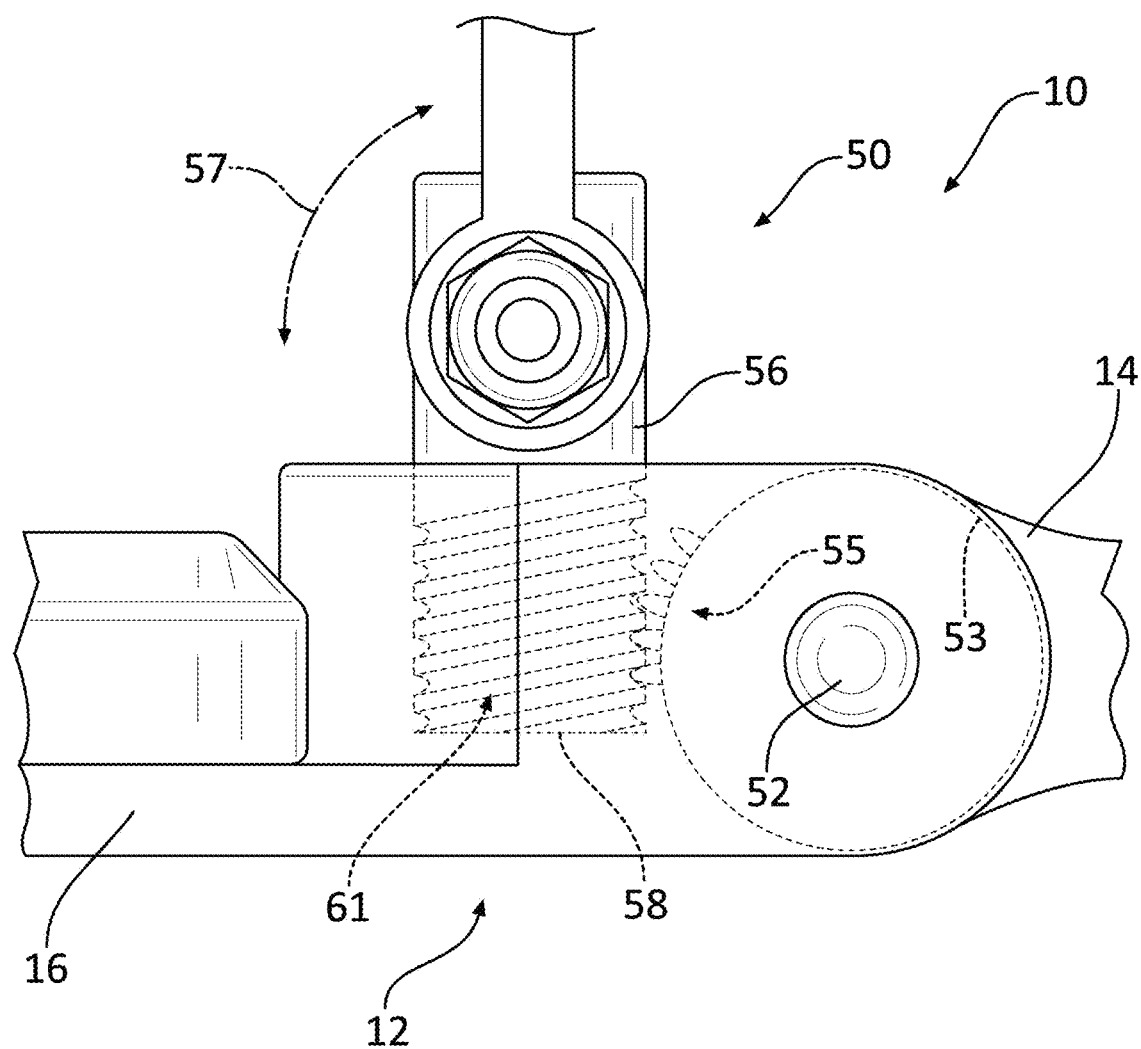
FIG. 10 is a detailed side perspective view of a joint for a knee brace apparatus, according to some embodiments of the present disclosure.
Figure 11:
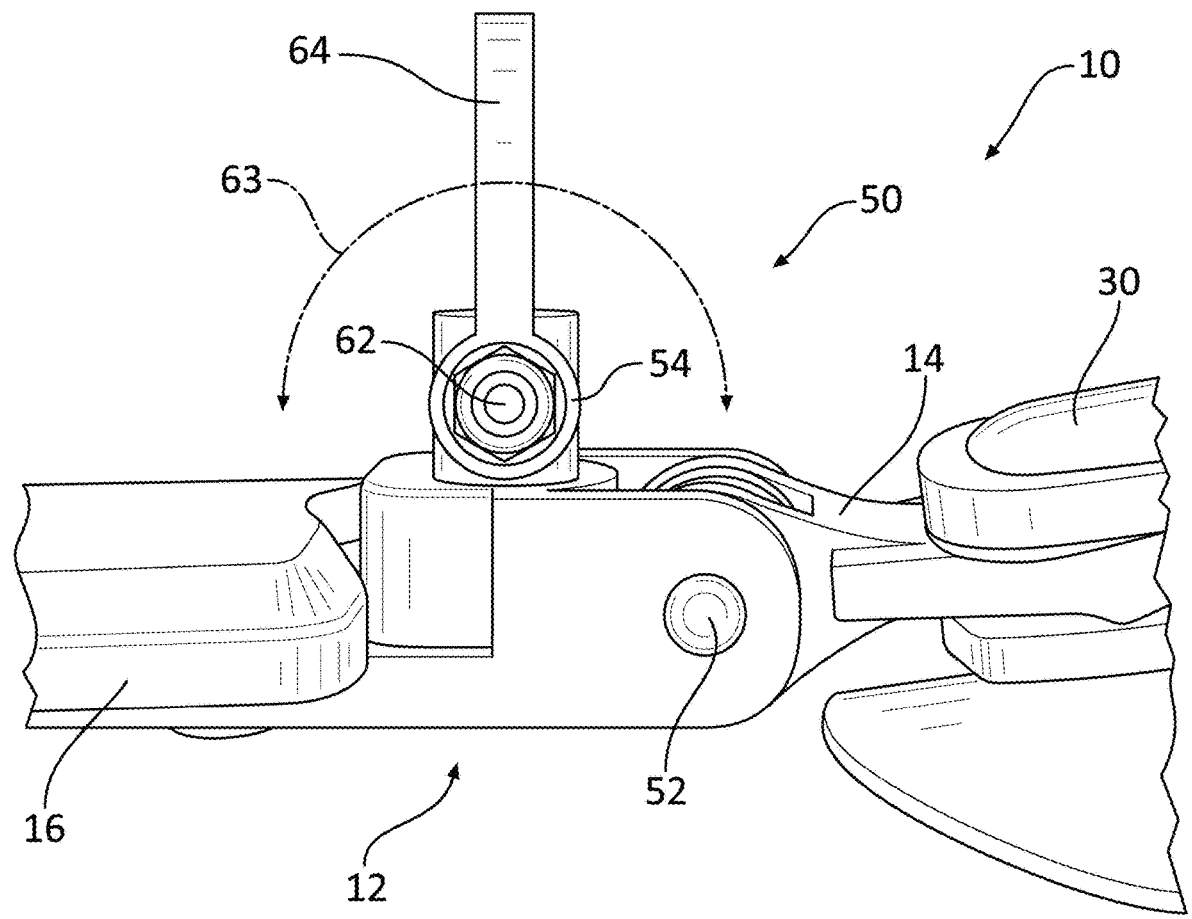
FIG. 11 is a detailed side perspective view of a manual adjustment tab for a knee brace apparatus, according to some embodiments of the present disclosure.
Figure 12:
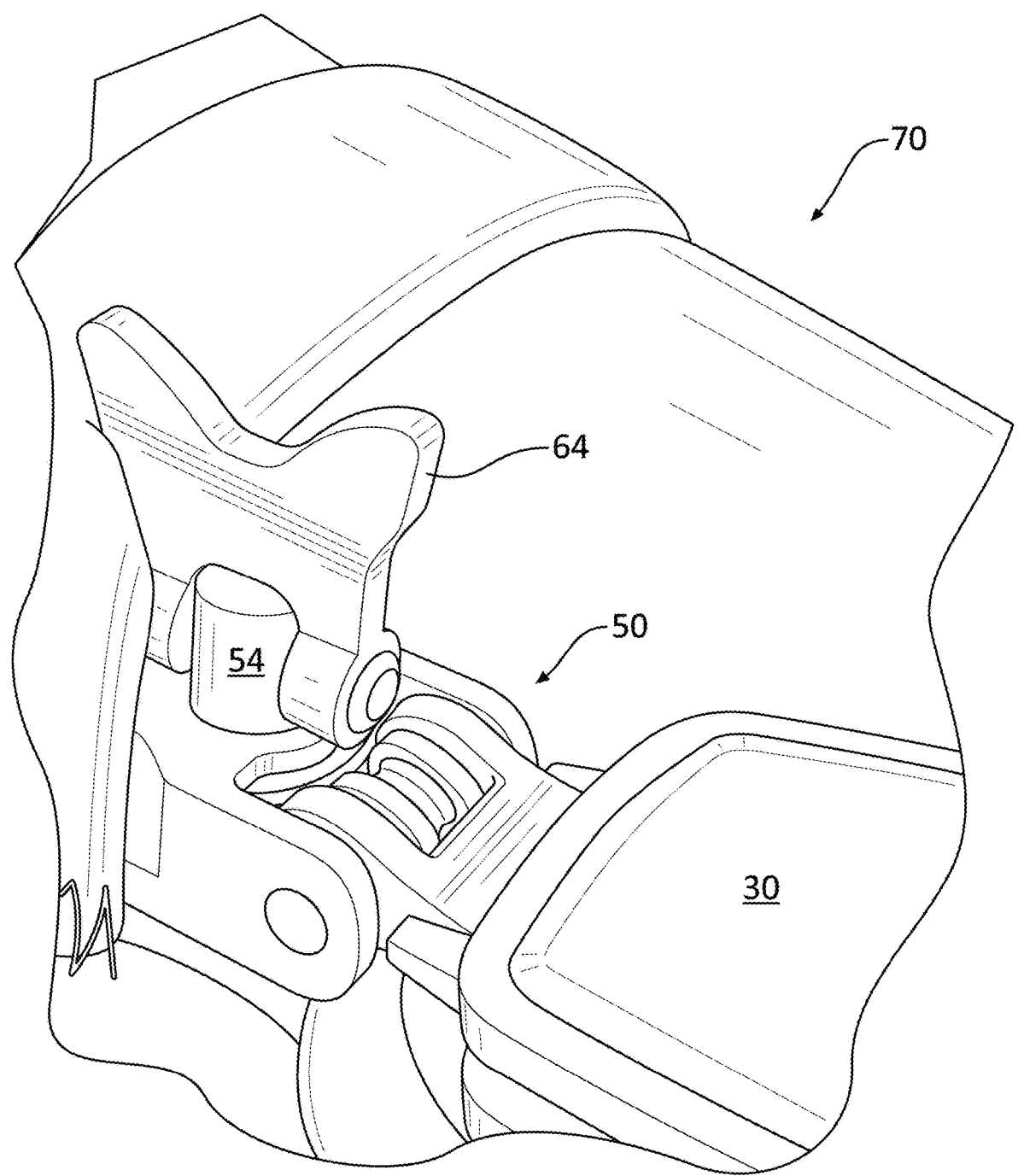
FIG. 12 is a detailed perspective view of a manual adjustment tab for a knee brace apparatus, according to some embodiments of the present disclosure.
Figure 13:
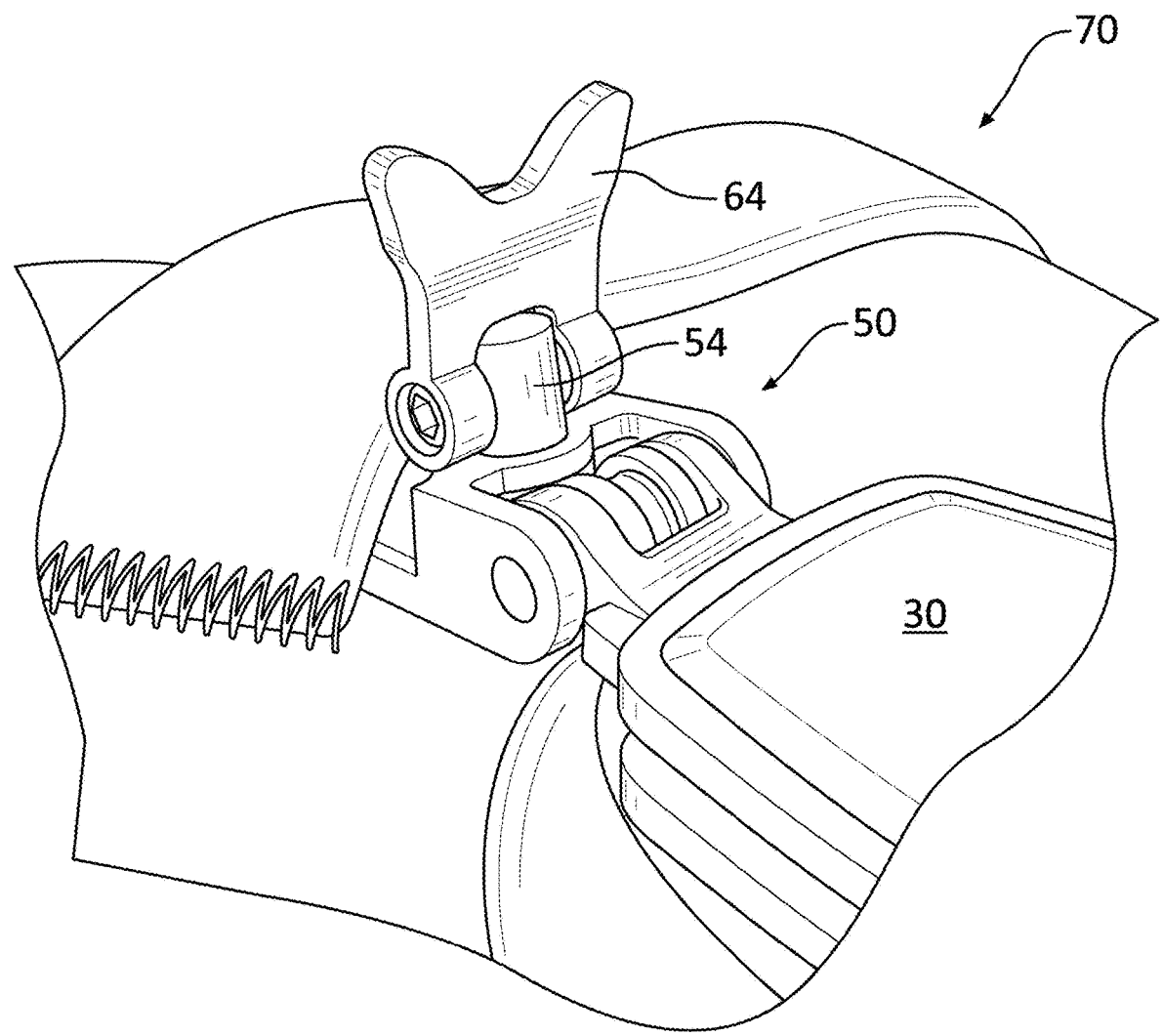
FIG. 13 is a detailed perspective view of a manual adjustment tab for a knee brace apparatus, according to some embodiments of the present disclosure.

Referring now to FIGS. 9-10, the first pin 54 is shown, according to some embodiments of the present disclosure. In some embodiments, the first pin 54 is disposed on the first strut 12. As mentioned above, the first joint 50 may be operated (e.g., to pivot the distal portion 16 of the first strut 12 along the curvatures 51 or 53 depicted with reference to FIGS. 7-8) via the first pin 54. In particular, the first joint 50 may include a hub 53, which may be mechanically engaged with the first pin 54. For example, and as shown with reference to FIG. 10, the hub 53 may feature a first set of teeth 55. The first set of teeth 55 on the hub 53 may correspond to, and be mechanically engaged with, a first set of threading 61 on the first pin 54.

Referring now to FIGS. 9-10, the first pin 54 is shown, according to some embodiments of the present disclosure. As suggested above, the first pin 54 may be disposed on the first strut 12 and mechanically engaged with the first joint 50 (the hub 53, in particular), allowing the first pin 54 to operate the first joint 50. For example, the first pin 54 may include a proximal portion 58 mechanically engaged with the first joint 50, as well as a distal portion 56. The proximal portion 58 of the first pin 54 may include the first set of threading 61 which corresponds to, and is mechanically engaged with, the first set of teeth 55 on the hub 53 of the first joint 50. The distal portion 56 of the first pin 54 may project off of the first strut 12 and thus, as depicted with reference to FIG. 1, free of the sleeve 70. Accordingly, the distal portion 56 of the first pin 54 may be manually operated by a user in order to pivot the distal portion 16 of the first strut 12 about the first anteroposterior axis 500 relative to the first joint 50.

In some embodiments, and as depicted with reference to FIG. 9, the first pin 54 is rotatable in either direction along a curvature 51 (e.g., by manual rotation via the distal portion 56 of the first pin 54). As the first pin 54 is rotated in either direction along the curvature 51, the first set of threading 61 on the proximal portion 58 of the first pin 54 may be rotated relative to the first set of teeth 55 on the hub 53 of the first joint 50, thereby causing the first pin 54 to rotate in either direction along a curvature 57 as depicted with reference to FIG. 10. For example, the first pin 54 may be secured on the distal portion 16 of the first strut 12 such that while the first pin 54 is permitted to rotate, the first pin 54 is secured in all other directions with respect to the distal portion 16 of the first strut 12. Accordingly, as the first pin 54 moves in either direction along the curvature 57, the distal portion 16 of the first strut 12 may correspondingly be pivoted along the curvature 57 relative to the anteroposterior pivot point 52 of the first joint 50, such that the distal portion 16 of the first strut 12 may be pivoted about the first anteroposterior axis 500 depicted with reference to FIG. 1. Thus, the first pin 54 may be rotated relative to the first joint 50, such that the mechanical engagement between the first pin 54 and the first joint 50 effectuates pivoting the distal portion 16 of the first strut 12 about the first anteroposterior axis 500. As described in greater detail below, the first pin 54 may be manually operated by a user via a first cross-bar 62 disposed on the first pin 54 and a first manual adjustment tab 64 disposed on the first cross-bar 62.

Referring now to FIGS. 6, 9, and 11-12, the first cross-bar 62 and the first manual adjustment tab 64 are shown, according to some embodiments of the present disclosure. As mentioned above, the first cross-bar 62 may be disposed on the first pin 54. For example, the first pin 54 may include a hole extending perpendicular to a central axis 59 (depicted with reference to FIG. 6) defined by the first pin 54 (e.g., extending from the proximal portion 58 of the first pin 54 to the distal portion 56 of the first pin 54), and the first cross-bar 62 may be rotatably disposed therein. Accordingly, the cross-bar 62 may extend perpendicular to the central axis 59 of the first pin 54. The first manual adjustment tab 64, in turn, may be disposed on the first cross-bar 62, such that the first manual adjustment tab 64 is configured to be pivotable about the hole in the first pin 54. In this sense, the first manual adjustment tab 64 may be pivotable about the cross-bar 62 (or, more particularly, the hole in the first pin 54) along a curvature 63 as depicted with reference to FIG. 11. As a first example, the first manual adjustment tab 64 may be pivoted to lay flat against the distal portion 16 of the first strut 12, as depicted with reference to FIG. 9. As a second example, the first manual adjustment tab 64 may be pivoted to lay flat against the proximal portion 14 of the first strut 12 and/or the first joint 50, as depicted with reference to FIGS. 14 and 15. As a third example, the first manual adjustment tab 64 may be oriented away from the apparatus 10 (and therefore extending away from the sleeve 70), as depicted with reference to FIGS. 6 and 11-13.

Figure 14:
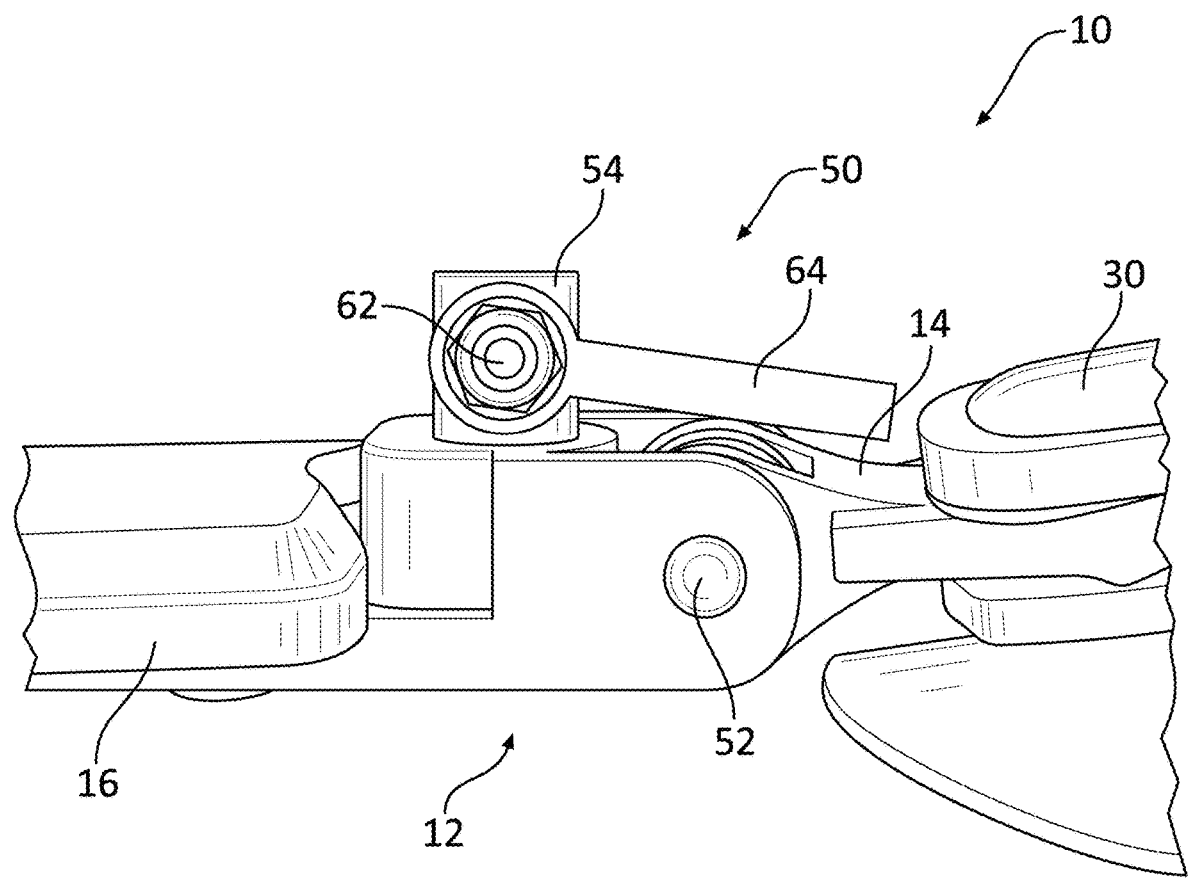
FIG. 14 is a detailed side perspective view of a manual adjustment tab for a knee brace apparatus, according to some embodiments of the present disclosure.
Figure 15:
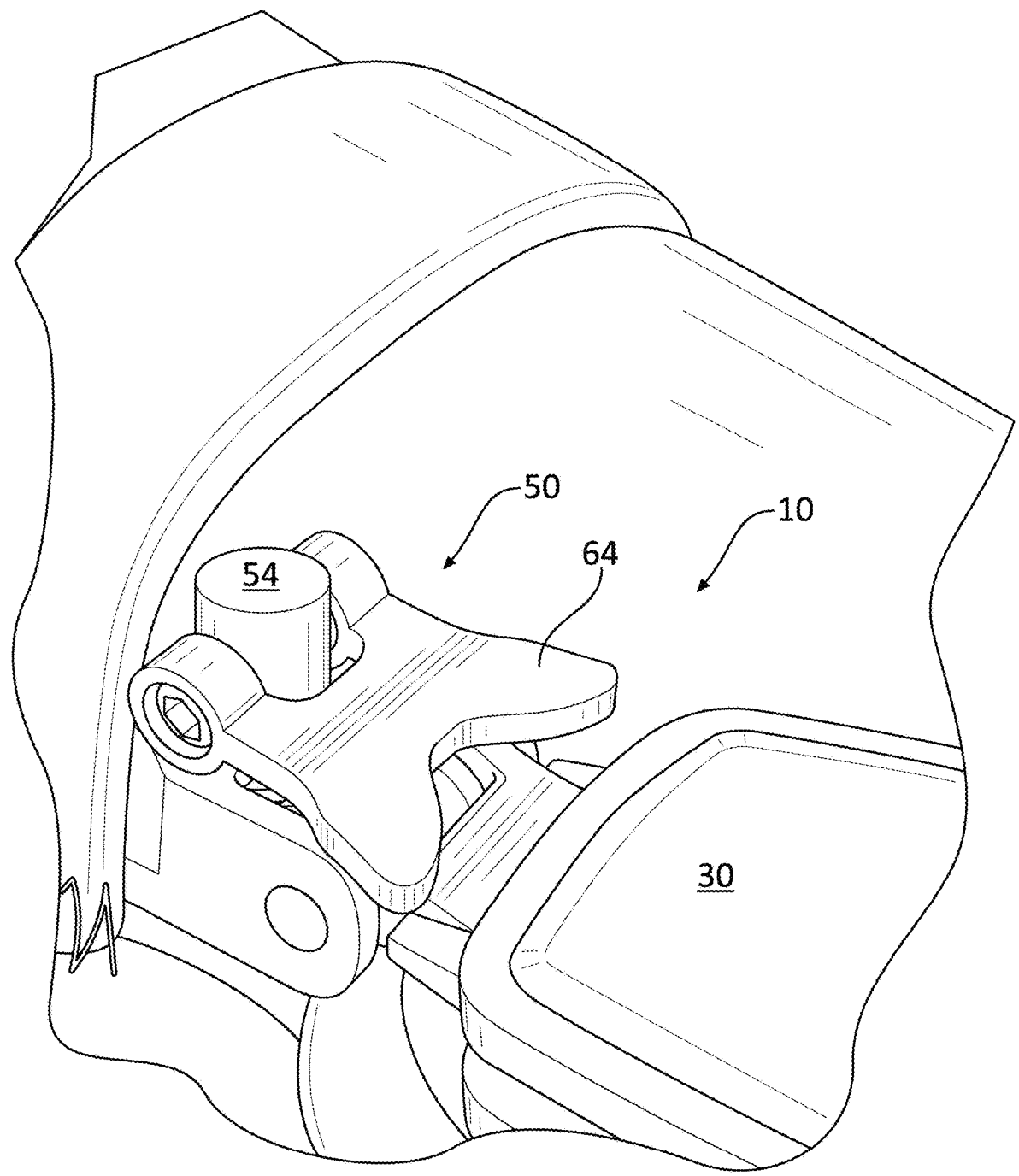
FIG. 15 is a detailed side perspective view of a manual adjustment tab for a knee brace apparatus, according to some embodiments of the present disclosure.

Advantageously, such pivotal adjustment of the first manual adjustment tab 64 may facilitate manual adjustment of the first pivot 50. For example, a user may handle the first manual adjustment tab 64 to be oriented as depicted with reference to FIGS. 6 and 11-13 and twist the manual adjustment tab 64, as shown by the transition of the depicted position of the first manual adjustment tab 64 between FIGS. 12 and 13. Such twisting of the manual adjustment tab 64 may rotate the first pin 54 along the curvature 51 as depicted with reference to FIG. 9, thereby operating the first joint 50 to pivot the distal portion 16 of the first strut 12. After the user has adjusted the first joint 50, the first manual adjustment tab 64 may be handled to be laid flat as depicted in FIGS. 9 and 14-15. Beneficially, the first manual adjustment tab 64 may provide a means for a user to adjust a varus or valgus pressure or adjustment provided by the assembly 100 without the need for additional tools and, in some cases, without removing the assembly 100 from the leg 200.

Figure 16:
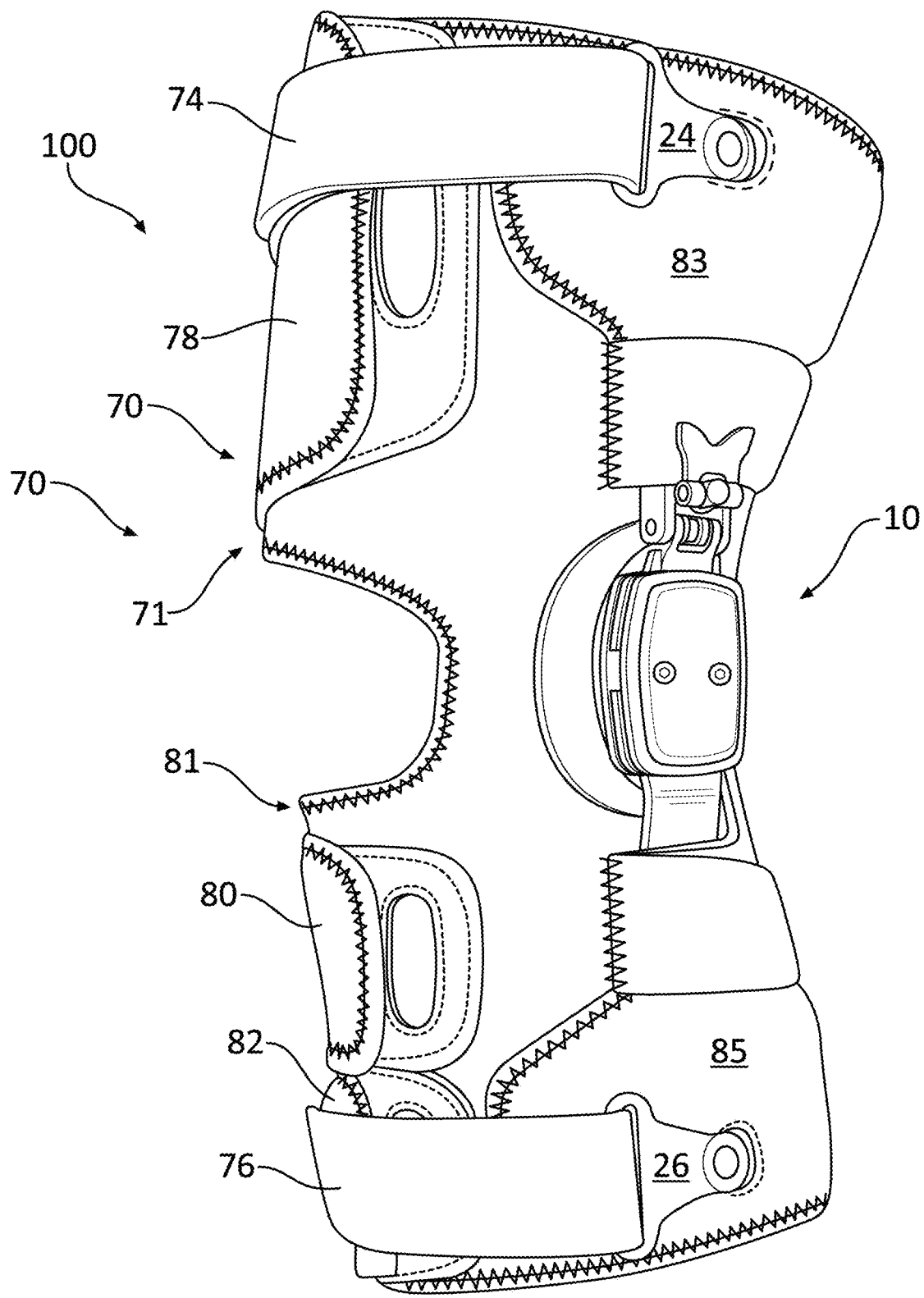
FIG. 16 is a side perspective view of a knee brace apparatus, according to some embodiments of the present disclosure.

Referring now to FIG. 16, the sleeve 70 is shown in greater detail, according to some embodiments of the present disclosure. As mentioned above, the sleeve 70 may include various folds, straps, and other fasteners that secure the first cuff 71 of the sleeve 70 to the thigh 202 and the second cuff 81 of the sleeve 70 to the calf 206. Such straps may include the first strap 74, which may secure the first cuff 71 to the thigh 202 by being secured within the first hook 24. Similarly, such straps may include the second strap 76, which may secure the second cuff 81 to the calf 206 by being secured within the second hook 26. In some embodiments, the sleeve 70 further includes a first (e.g., upper) fastener 78 (over which the first strap 74 may be secured), as well as a second (e.g., first lower) fastener 80 and a third (e.g., second lower) fastener 82 (over which the second strap 76 may be secured). The first fastener 78 may be configured to further secure (in conjunction with the first strap 74) the first cuff 71 to the thigh 202, while the second and third fasteners 80, 82 may be configured to further secure (in conjunction with the second strap 76) the second cuff 81 to the calf 206.

Referring now to FIGS. 17-24, a process of securing the assembly 100 to the leg 200 is shown, according to some embodiments of the present disclosure. While the leg 200 is not depicted in FIGS. 17-24, it should be appreciated that in order to secure the assembly 100 to the leg 200, the leg 200 may be positioned on an intermediate portion 72 (depicted with reference to FIGS. 17-18) of the sleeve 70 before conducting the steps for securing the assembly 100 as discussed below.

Figure 17:
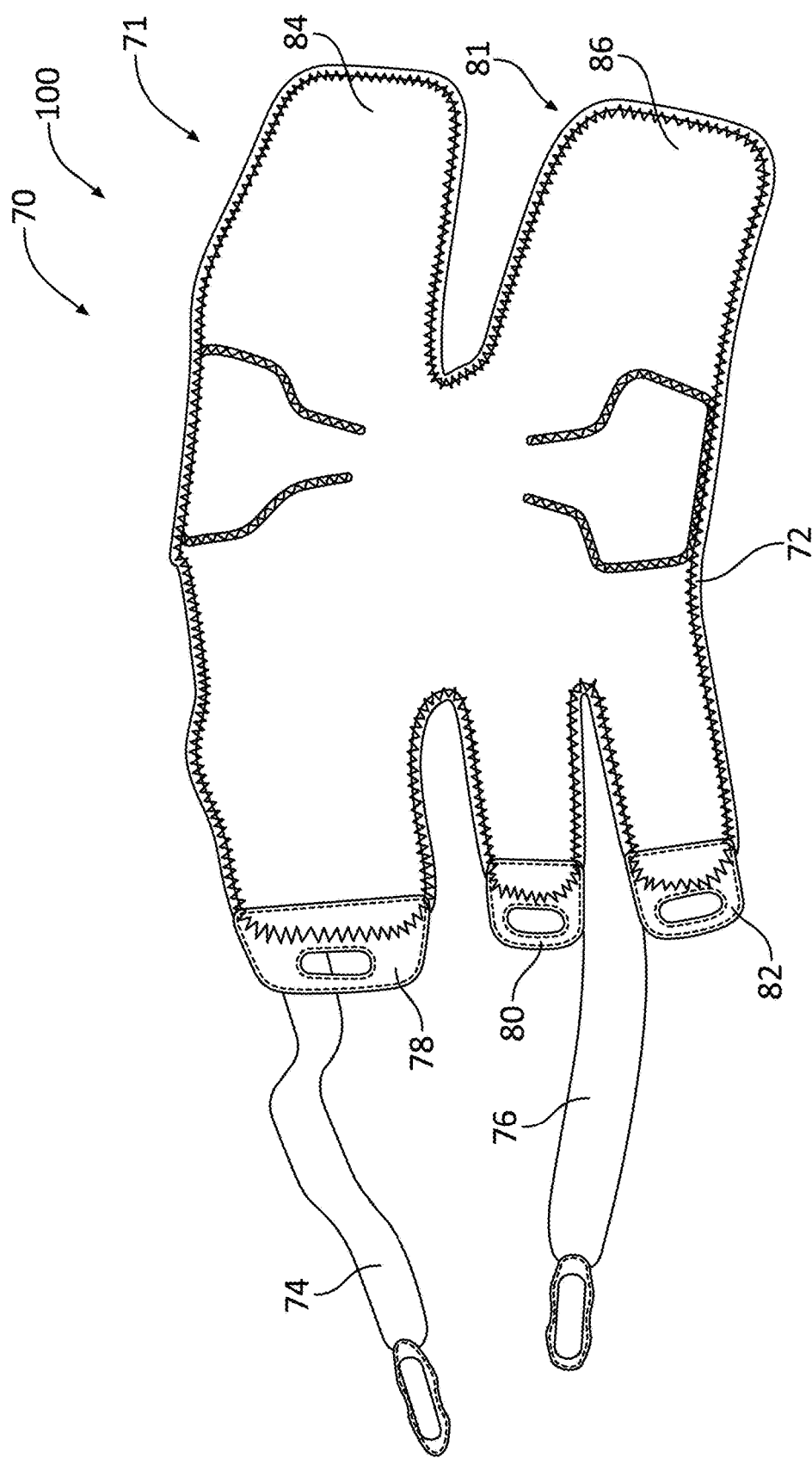
FIG. 17 is a rear perspective view of an opened sleeve for a knee brace apparatus, according to some embodiments of the present disclosure.
Figure 18:
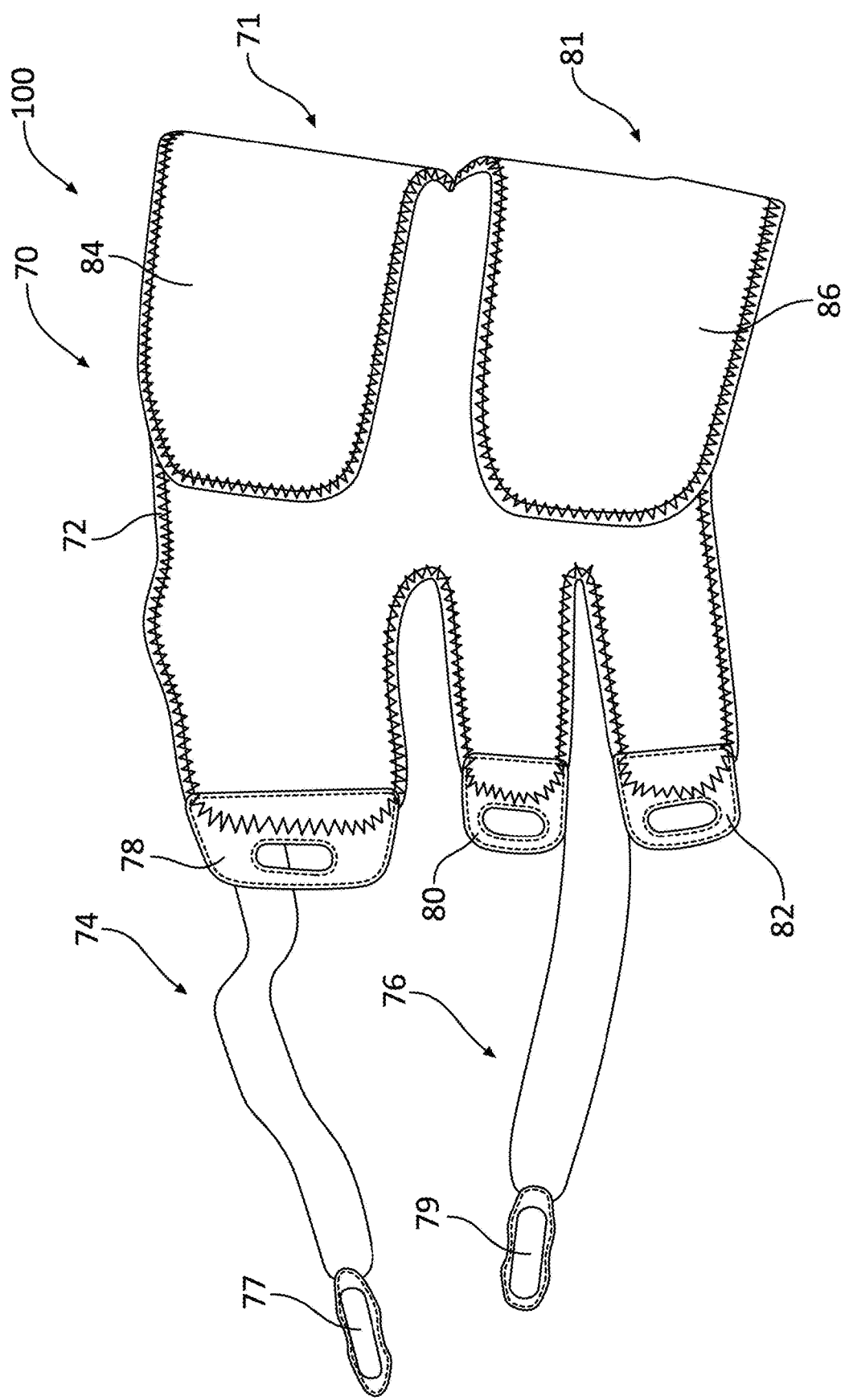
FIG. 18 is a rear perspective view of a partially opened sleeve for a knee brace apparatus, according to some embodiments of the present disclosure.
Figure 19:
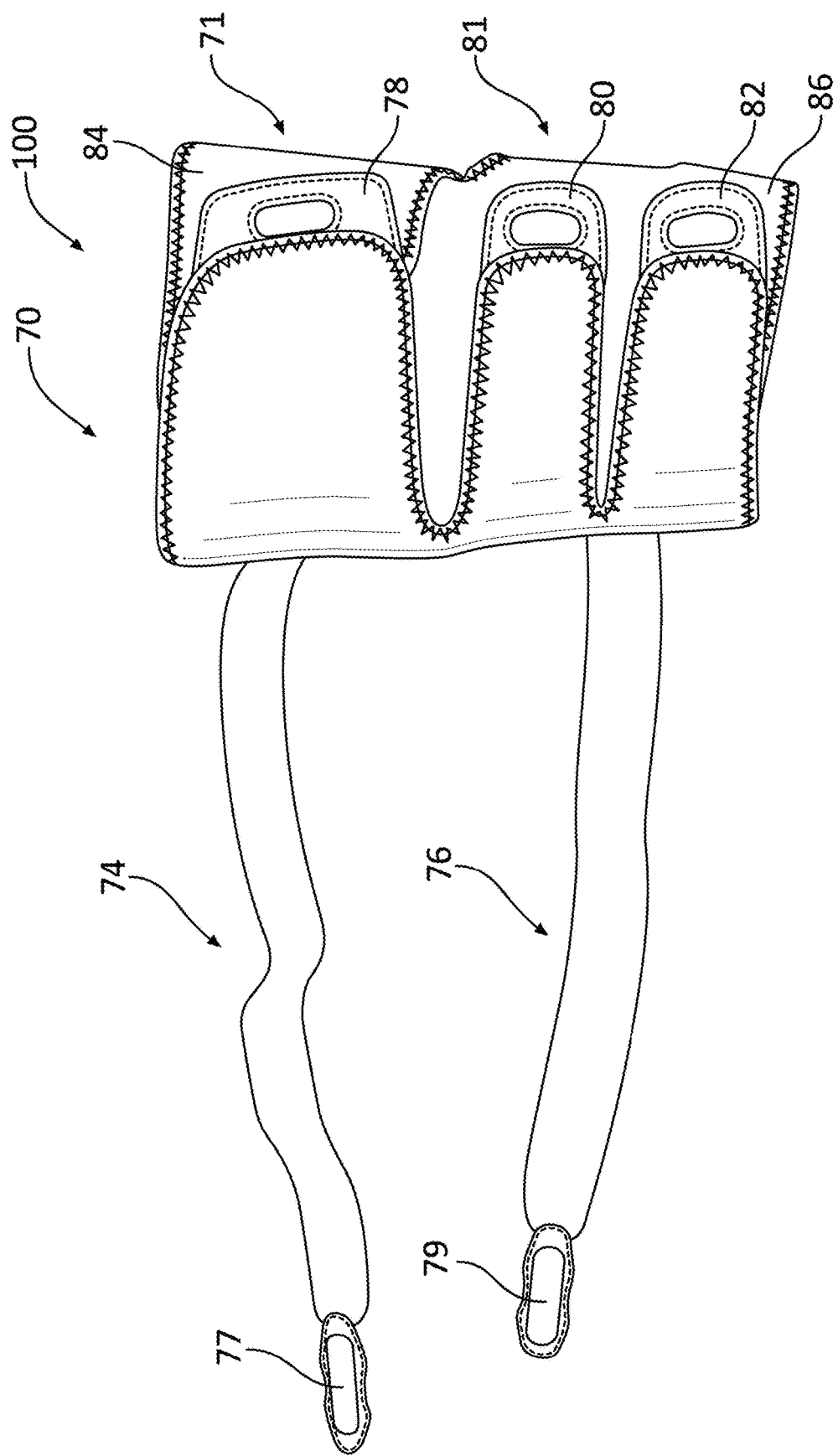
FIG. 19 is a rear perspective view of a closed sleeve for a knee brace apparatus, according to some embodiments of the present disclosure.
Figure 20:
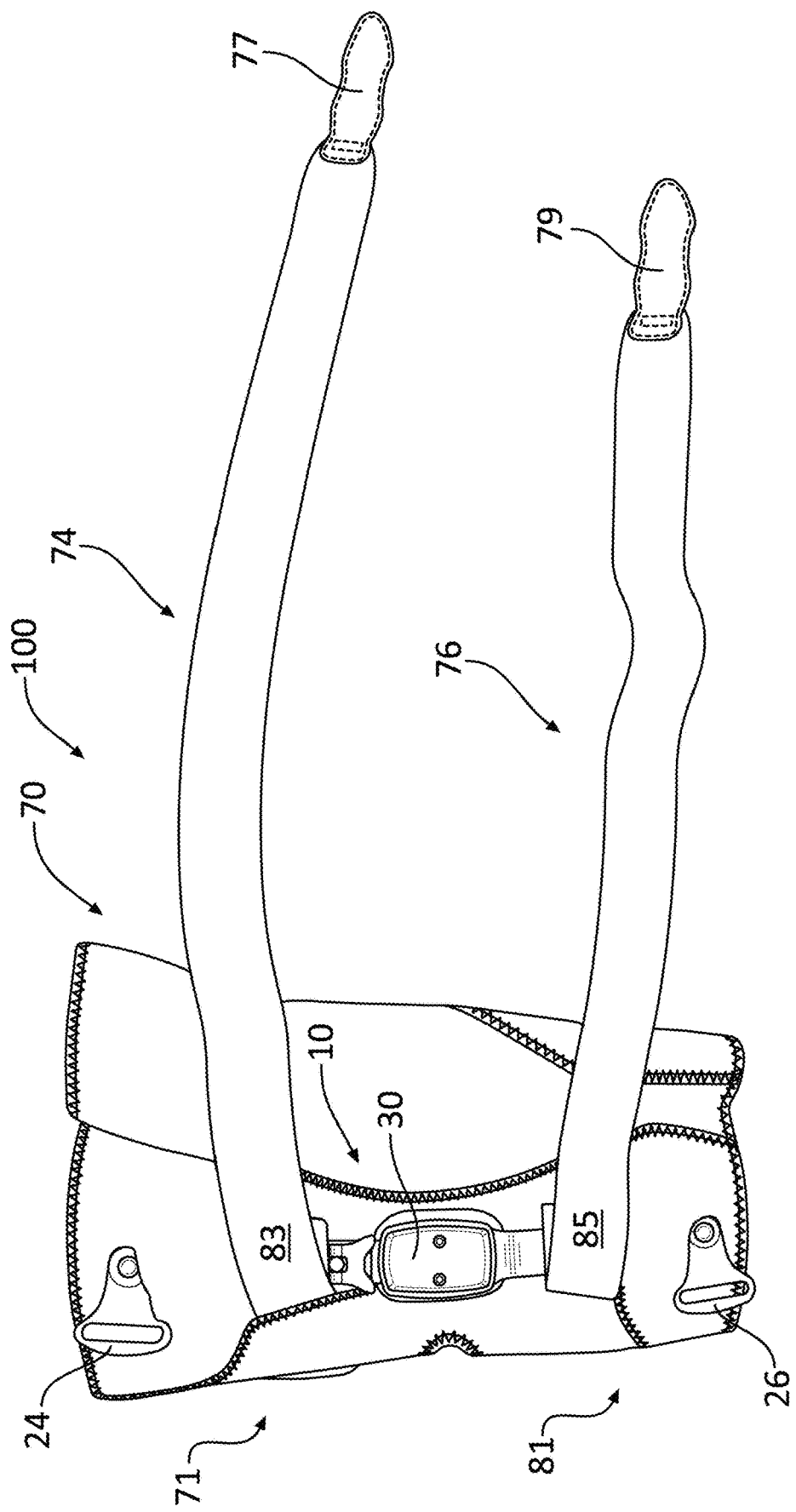
FIG. 20 is a front perspective view of a closed sleeve for a knee brace apparatus, according to some embodiments of the present disclosure.
Figure 21:
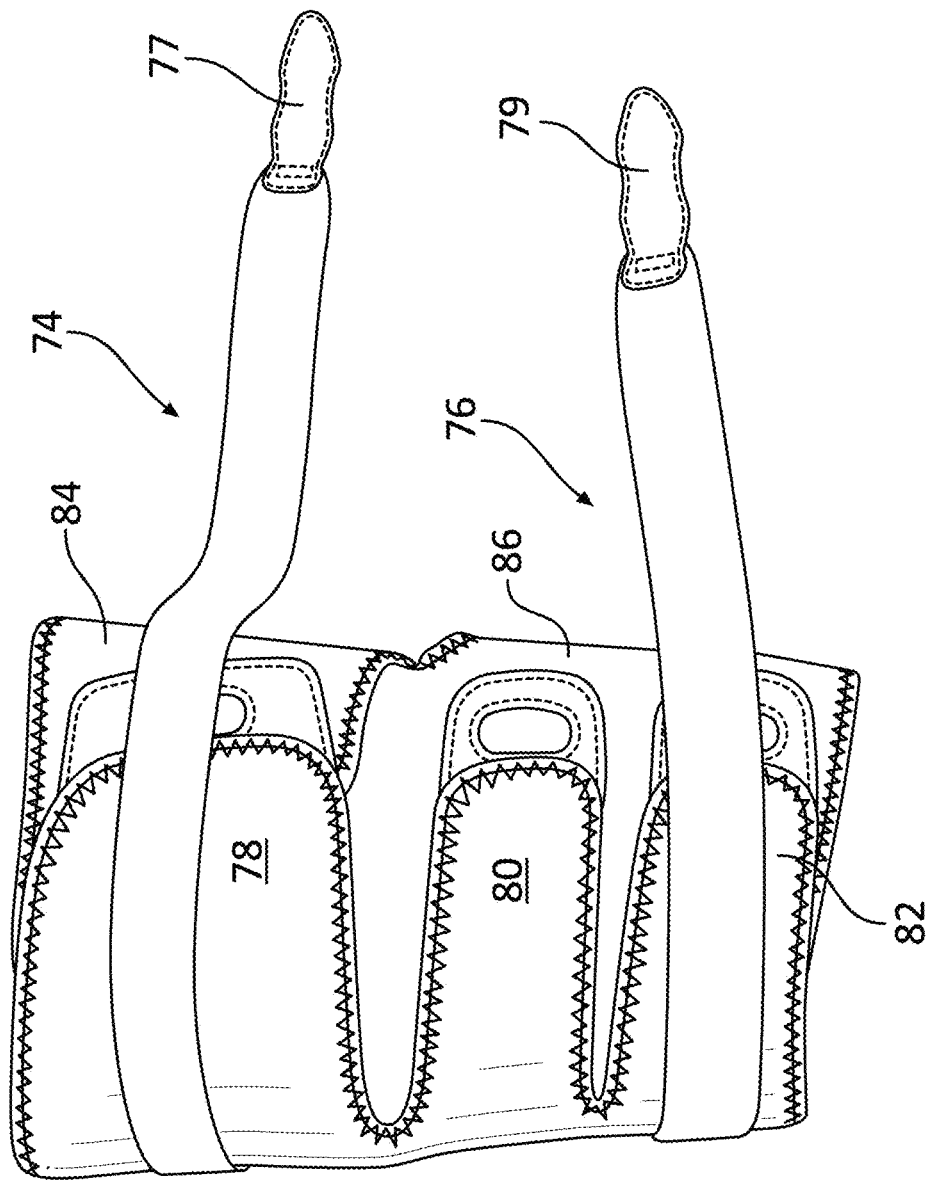
FIG. 21 is a rear perspective view of straps being folded over a closed sleeve for a knee brace apparatus, according to some embodiments of the present disclosure.
Figure 22:
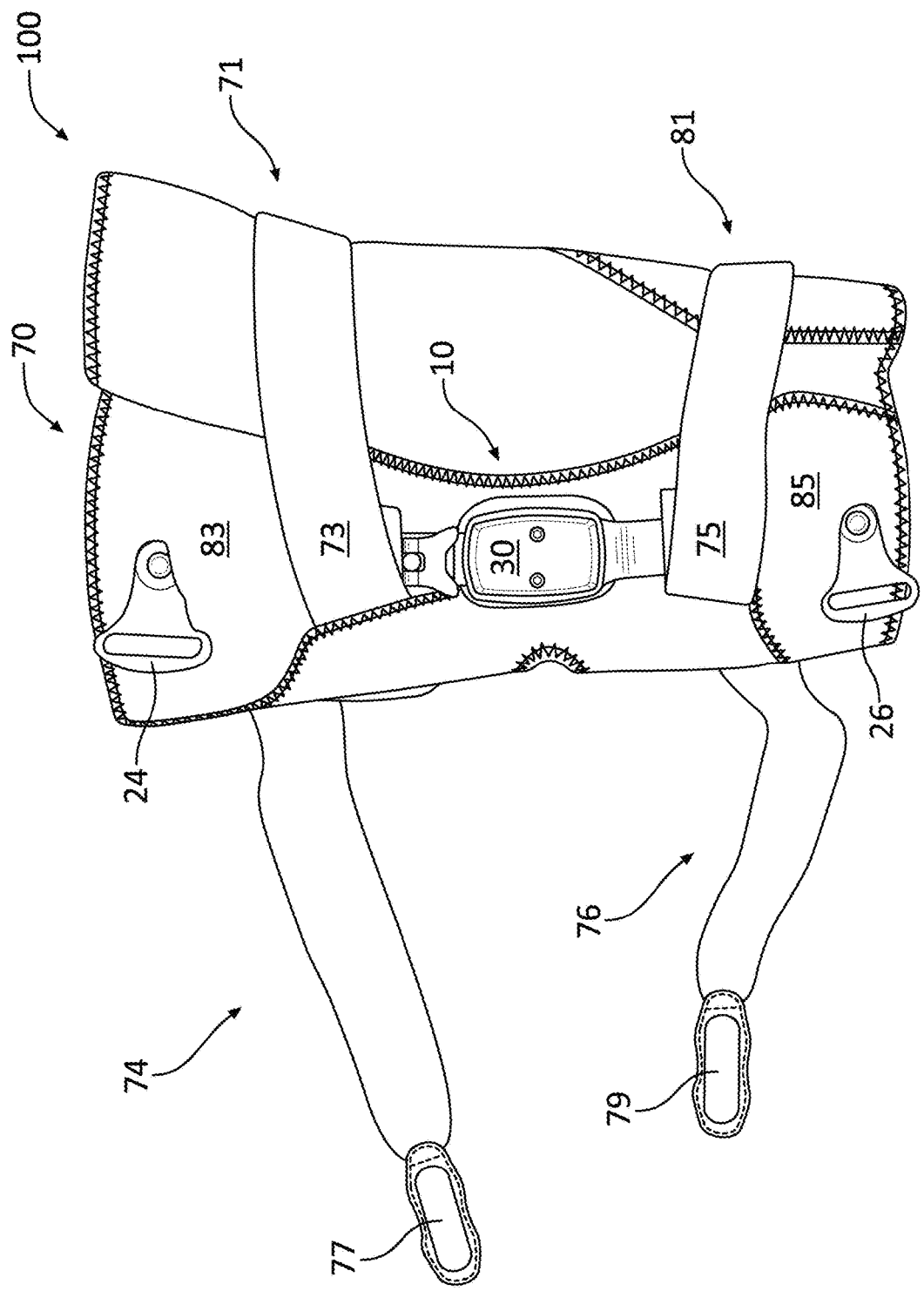
FIG. 22 is a front perspective view of straps being folded over a closed sleeve for a knee brace apparatus, according to some embodiments of the present disclosure.

Referring particularly to FIGS. 17-19, the first fastener 78 and the second and third fasteners 80, 82 may be secured to opposing portions of the sleeve 70. As a first example, a first (e.g., upper) tab 84 opposite the first fastener 78 may be folded over the intermediate portion 72 (as depicted with reference to the transition between FIGS. 17-18), and the first fastener 78, in turn, may be adhered to the first tab 84, as depicted with reference to FIG. 19. As a second example, a second (e.g., lower) tab 86 opposite the second and third fasteners 80, 82 may be folded over the intermediate portion 72 (as depicted with reference to the transition between FIGS. 17-18), and the second and third fasteners 80, 82, in turn, may be adhered to the second tab 86.

Referring particularly to FIGS. 20-24, the first and second straps 74, 76 may be secured to the sleeve 70. For example, the first and second straps 74, 76 may be secured to the sleeve 70 over the first fastener 78 and the second and third fasteners 80, 82 once such fasteners as secured as discussed above with reference to FIGS. 17-19. In some embodiments, and as discussed in greater detail below, the first and second straps 74, 76 are each wrapped around the entirety of the sleeve 70 in order to secure the assembly 100 to the leg 200. For example, the first strap 74 may be attached to the sleeve 70 at a first base 73 and the second strap 76 may be attached to the sleeve 70 at a second base 75. The first strap 74 may include a first strap end 77, and the second strap 76 may include a second strap end 79. The first and second straps 74, 76 may be configured to secure the sleeve 70 to the leg 200 by being wrapped in a first direction around the sleeve 70 (as depicted with reference to the transition between FIGS. 20-23) and guided through the first and second hooks 24, 26, respectively (as depicted with reference to FIG. 23).

Figure 23:
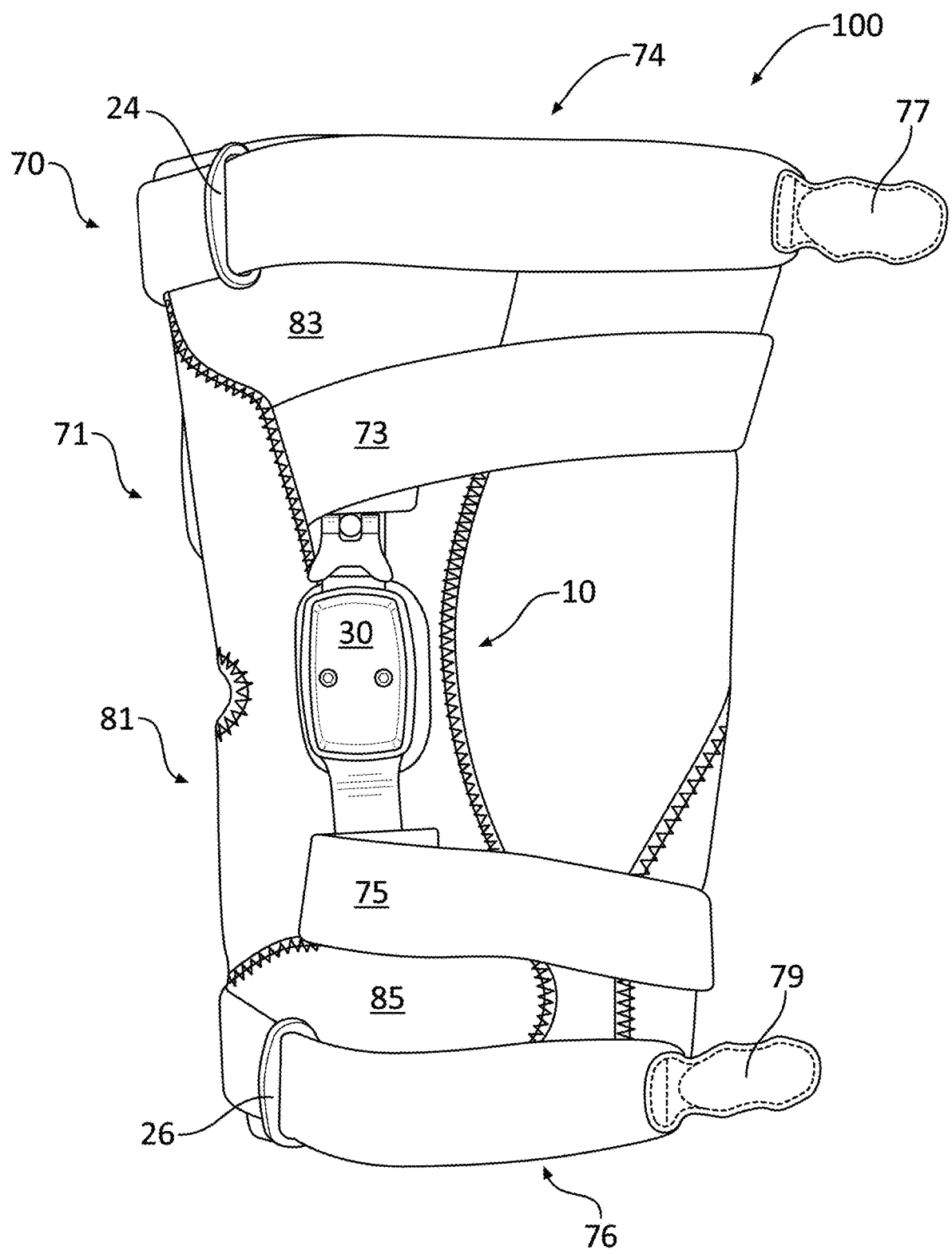
FIG. 23 is a front perspective view of straps being guided through hooks for a knee brace apparatus, according to some embodiments of the present disclosure.
Figure 24:
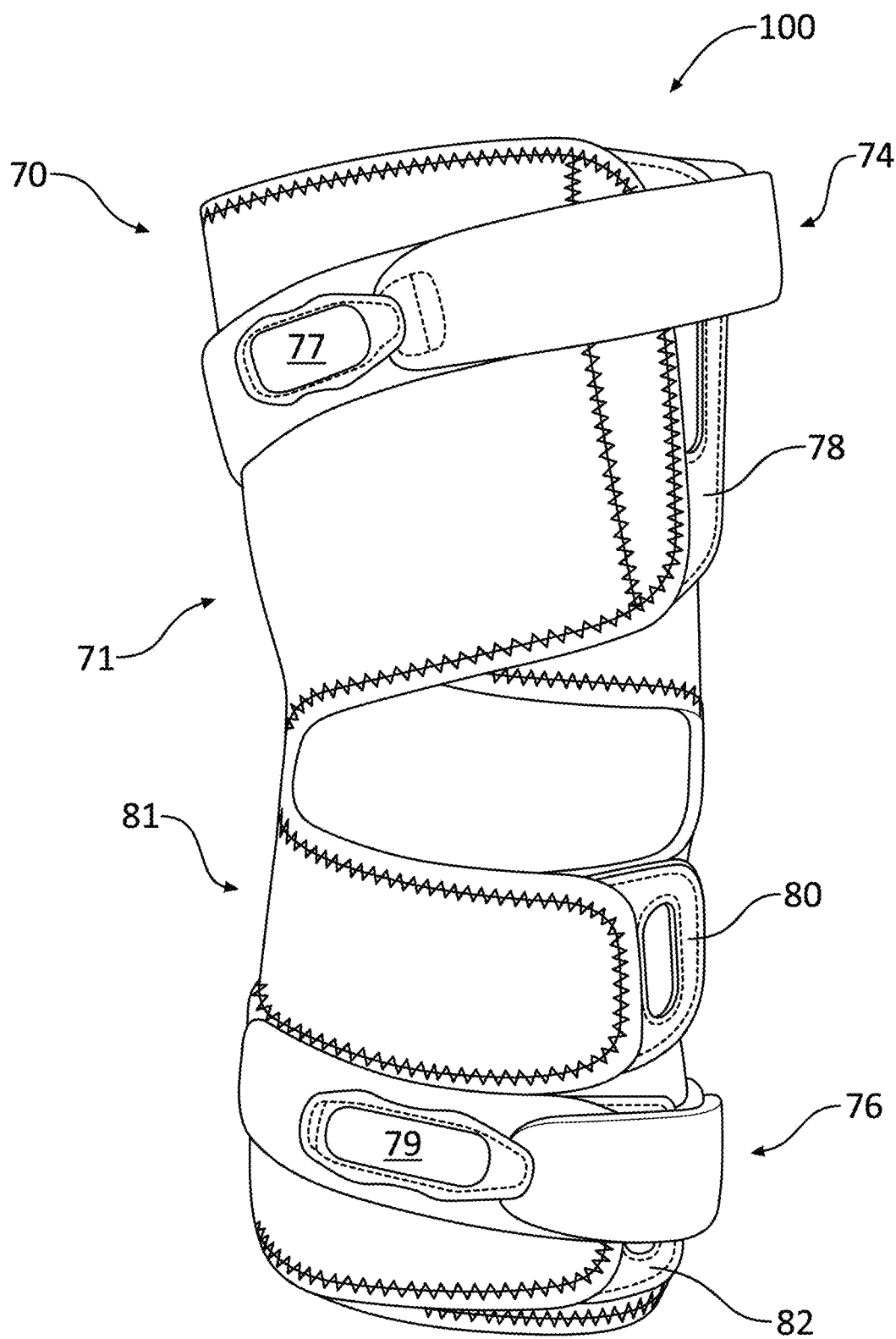
FIG. 24 is a side perspective view of straps being secured to a closed sleeve for a knee brace apparatus, according to some embodiments of the present disclosure.

As depicted with reference to the transition between FIGS. 23-24, the first and second straps 74, 76 may, after being guided thought the first and second hooks 24, 26 (respectively), be wrapped in a second direction opposite the aforementioned first direction, thereby pulling against the first and second hooks 24, 26 in the second direction. As depicted with reference to FIG. 24, the ends 77, 79 of the first and second straps 74, 76 (respectively) may then be adhered to the sleeve 70. As depicted with reference to FIG. 22, the first and second hooks 24, 26 may be positioned relative to the sleeve 70 further in the aforementioned first direction than the bases 73, 75 of the first and second straps 74, 76 (respectively). Accordingly, when the first and second strap ends 77, 79 are secured to the first and second hooks 24, 26 (respectively) and adhered to the sleeve 70 as depicted with reference to FIG. 24, the first and second straps 74, 76 are each wrapped around the entirety of the sleeve 70.

As mentioned above with reference to FIG. 2, the first and second hooks 24, 26 may be disposed on the distal portion 16 of the first strut 12 and the distal portion 22 of the second strut 18, respectively. The apparatus 10, of course, may be secured in place as discussed above. Thus, when the first and second straps 74, 76 are secured to the first and second hooks 24, 26 and adhered to the sleeve 70 as depicted with reference to FIG. 24, the first and second hooks 24, 26 of the base assembly 10 may each provide a secure base for using the first and second straps 74, 76 to secure the sleeve 70 to the leg 200.

Figure 25:
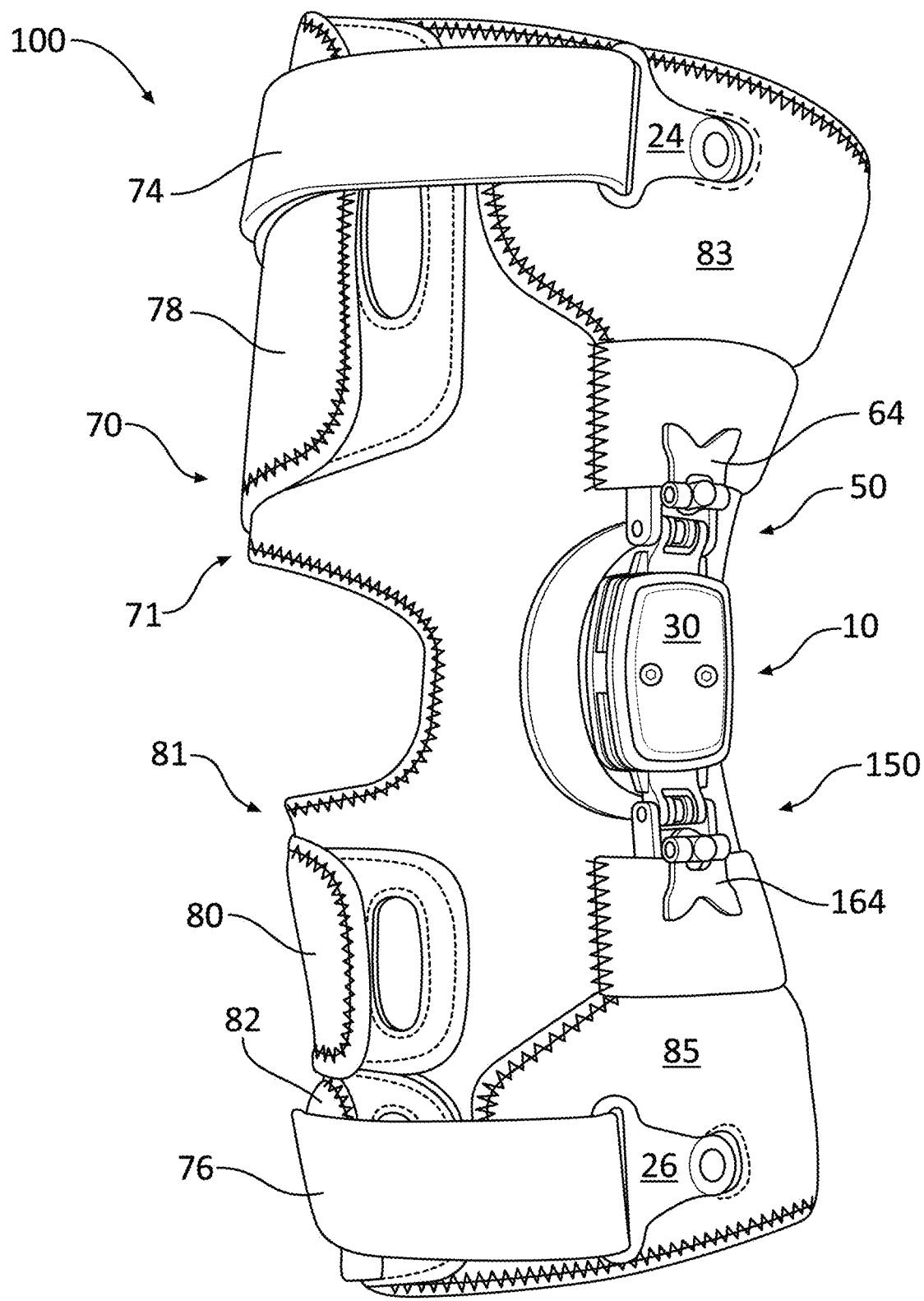
FIG. 25 is a side perspective view of a knee brace apparatus with two joints, according to some alternative embodiments of the present disclosure.

Referring now to FIG. 25, the apparatus 10 is shown with a second joint 150, according to some alternative embodiments of the present disclosure. For example, the second joint 150 may be disposed on the second strut 18, allowing at least a portion of the second strut 18 to pivot about a second anteroposterior axis defined by the second joint 150 (similar to the first anteroposterior axis 500 depicted with reference to FIG. 1, for example). In particular, the second joint 150 may connect the distal portion 20 of the second strut 18 to the proximal portion 22 of the second strut 18 and may be configured the same as, analogous to, or otherwise similar to, the first joint 50. Thus, the second joint 150 may include a second pin disposed on the second strut 18 and mechanically engaged with the second joint 150 (similar to the first pin 54), a second cross-bar disposed on the second pin (similar to the first cross-bar 62), and a second manual adjustment tab 164 disposed on the second cross-bar (similar to the first manual adjustment tab 64). Of course, the second joint 150 may include a second set of teeth (similar to the first set of teeth 55 on the first hub 53), and the second pin may include a corresponding second set of threading mechanically engaged with the second set of teeth. Advantageously, this may allow a greater or more articulate degree of varus or valgus pressure to be applied to the knee 204 of the leg 200.

Referring now to FIGS. 26-29, the first pin 54 may include a first tool fitting 66, which may be configured to facilitate operation of the first joint 50 (as discussed above) via a tool, according to some alternative embodiments of the present disclosure. For instance, the apparatus 10 may include the first pin 54, the first cross-bar 62, and the first manual adjustment tab 64 (which may operate as discussed above in terms of rotating the first pin 54 relative to the first joint 50), as well as the first tool fitting 66 disposed on the first pin 54 to facilitate additional methods for rotating of the first pin 54 via the tool.

Figure 26:
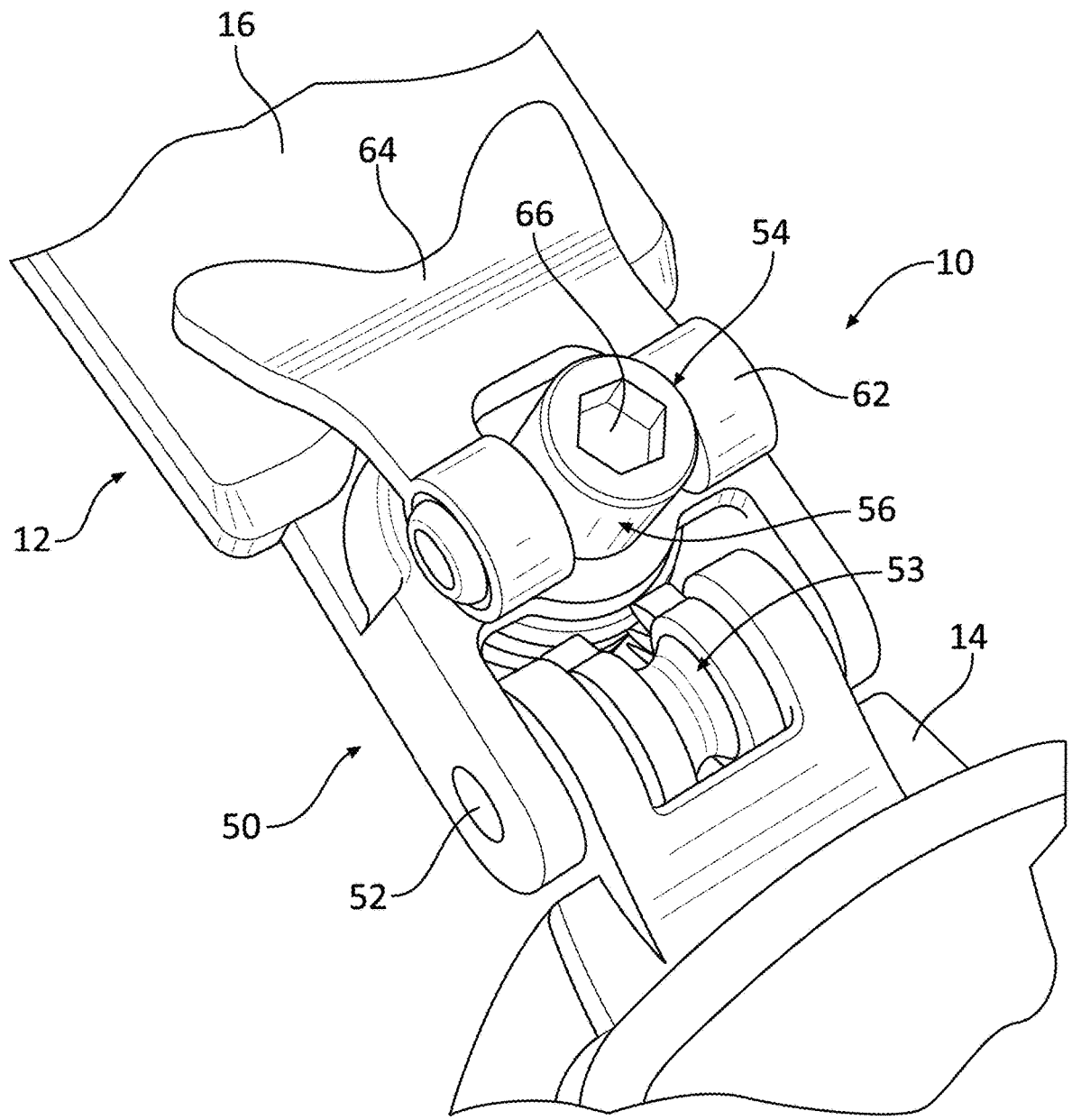
FIG. 26 is a detailed front perspective view of a joint for a knee brace apparatus with a tool fitting provided as a key-hole, according to some alternative embodiments of the present disclosure.
Figure 27:
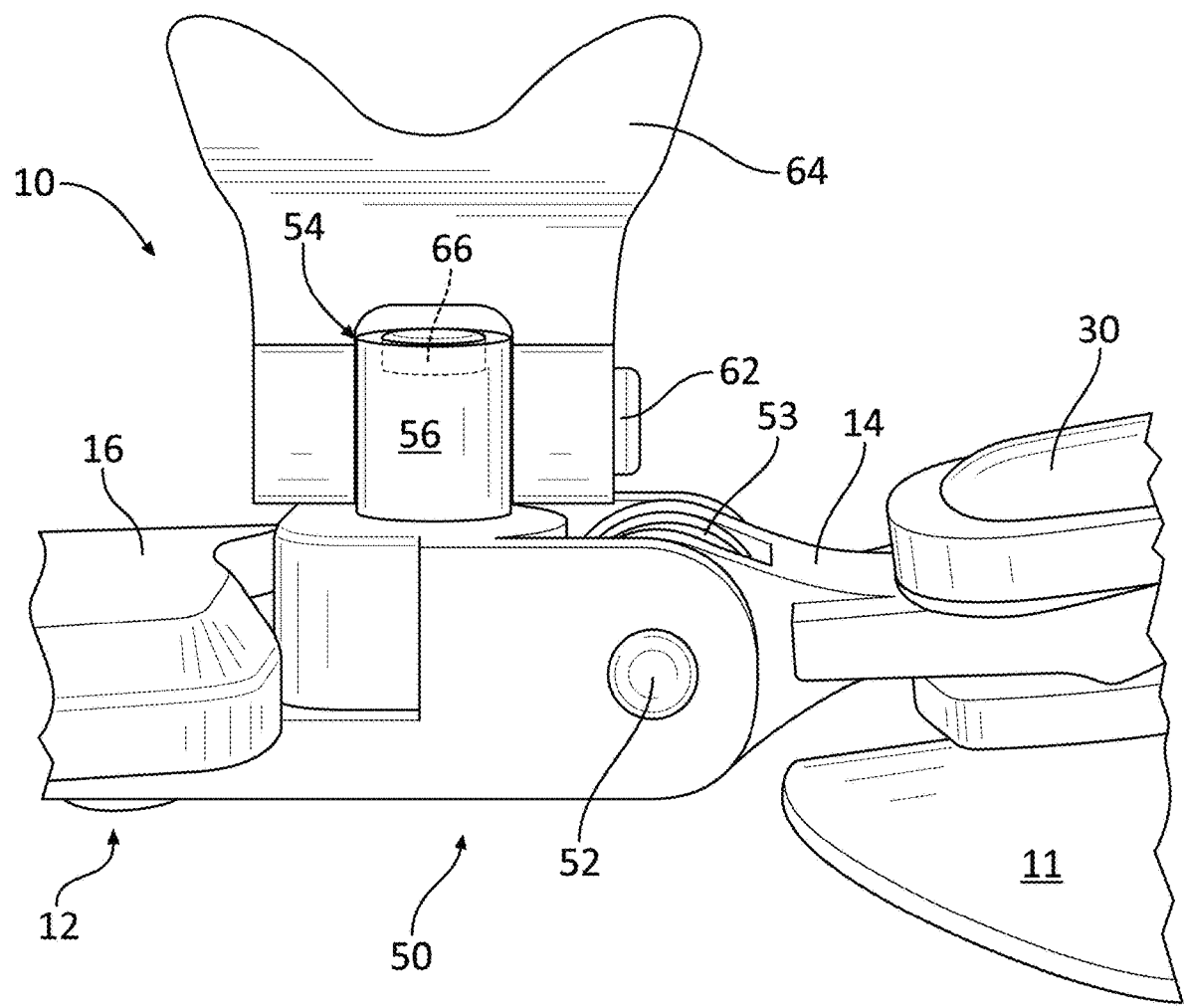
FIG. 27 is a detailed side perspective view of a joint for a knee brace apparatus with a tool fitting provided as a key-hole, according to some alternative embodiments of the present disclosure.
Figure 37:
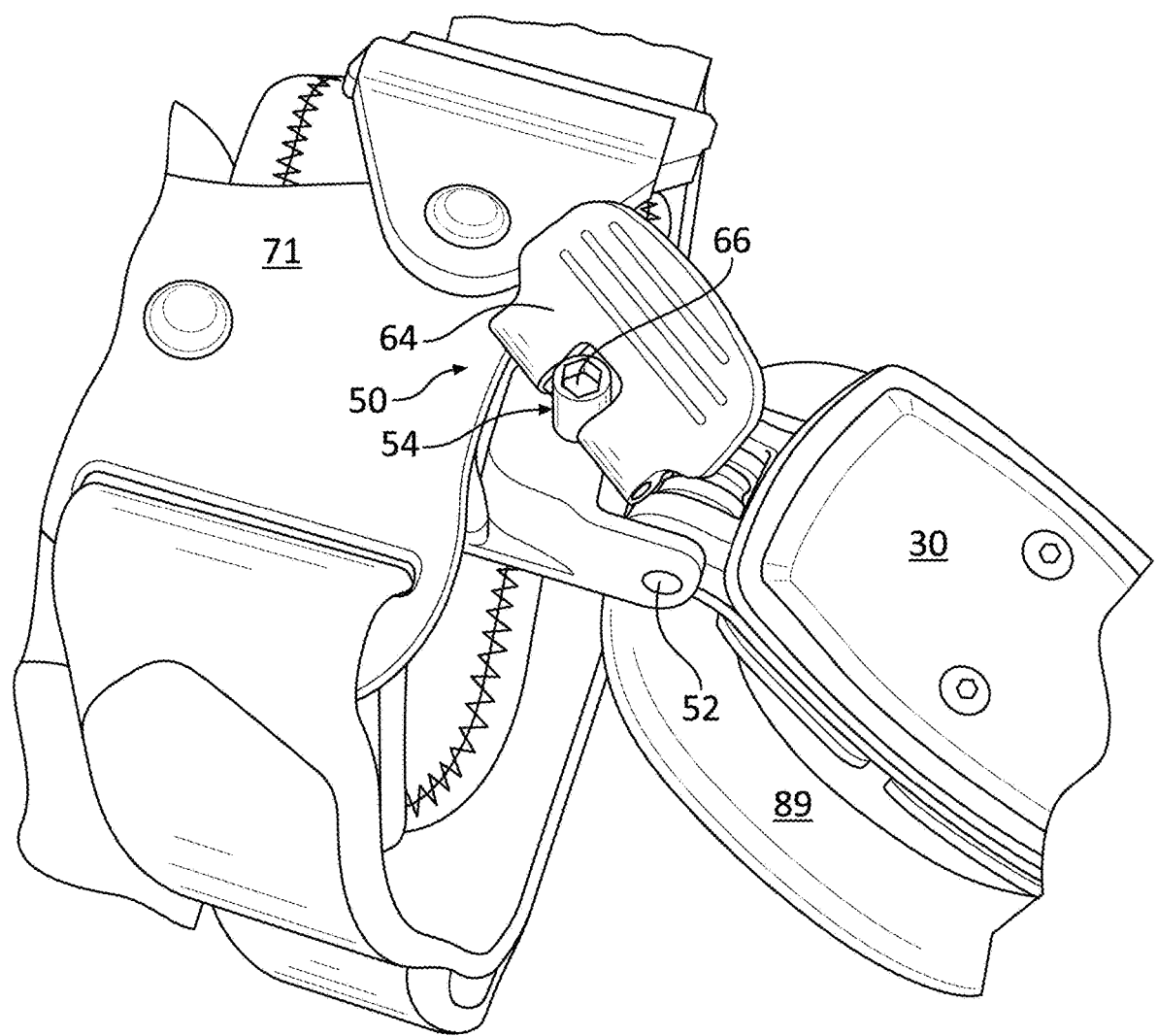
FIG. 37 is a side perspective view of a user operating a manual adjustment tab of a joint for a knee brace apparatus with a tool fitting, according to some alternative embodiments of the present disclosure.
Figure 38:
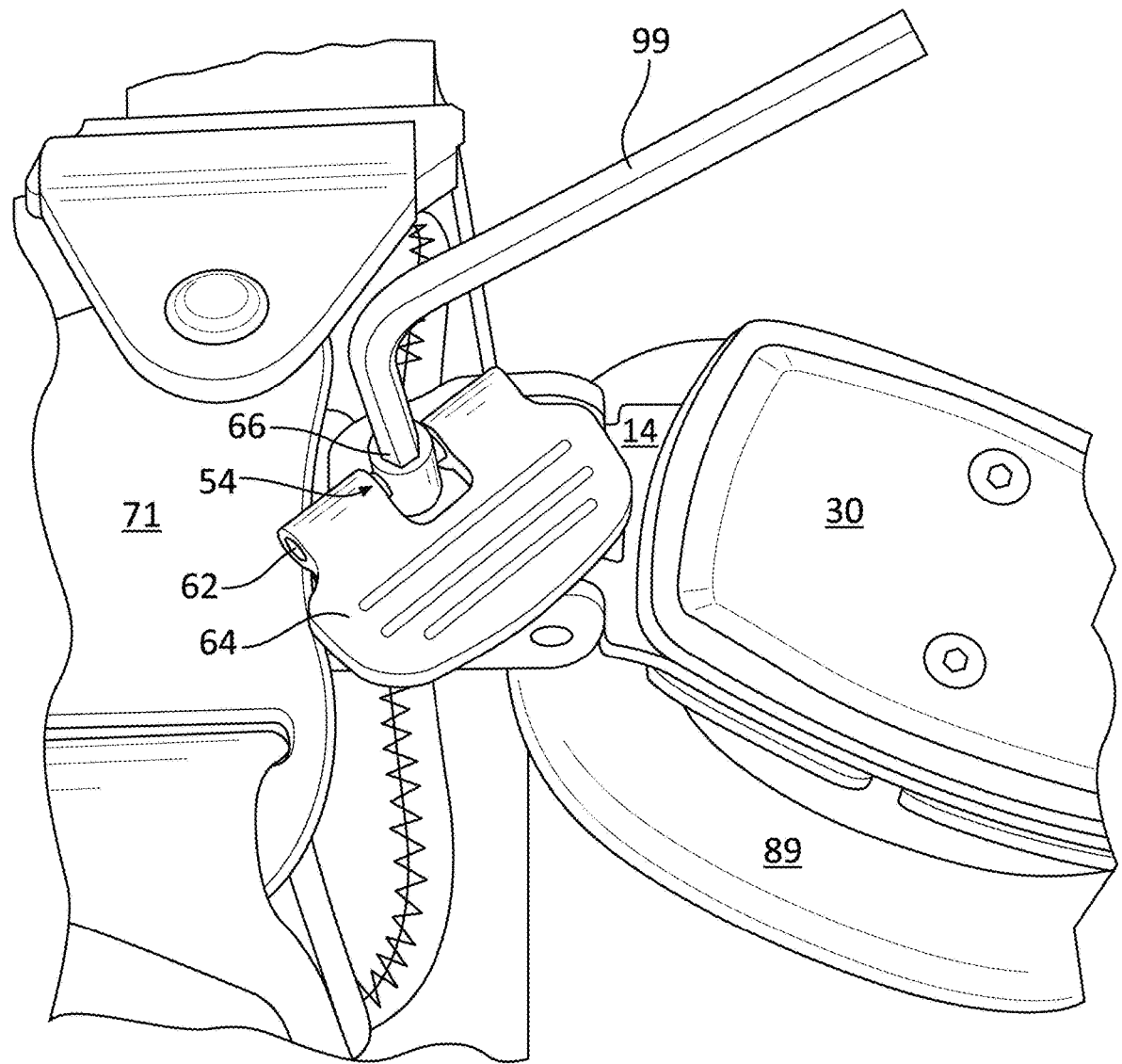
FIG. 38 is a side perspective view of a user operating a tool fitting of a joint for a knee brace apparatus, according to some alternative embodiments of the present disclosure.

As a first example, and as depicted with reference to FIGS. 26-27, the first tool fitting 66 may be a first key-hole. For instance, a top surface of the distal portion 56 of the first pin 54 may include the first tool fitting 66 provided as a first key-hole which extends into the top surface of the distal portion 56 of the first pin 54. In other words, the first tool fitting 66 may be a depression formed to receive the tool. In this sense, the first tool fitting 66, when provided as a first key-hole, may be a hex-socket configured to receive a tool, such as an Allen wrench 99 depicted with reference to FIG. 37. In other embodiments, the first tool fitting 66, when provided as a first key-hole, may be a depression shaped to receive a standard screw-driver, such as a Phillips-Head screwdriver, a flat-head screwdriver, and so on. Accordingly, the tool may be inserted into the first tool fitting 66 and rotated in order to rotate the first pin 54 and, in turn, operate the first joint 50 as discussed above.

Figure 28:
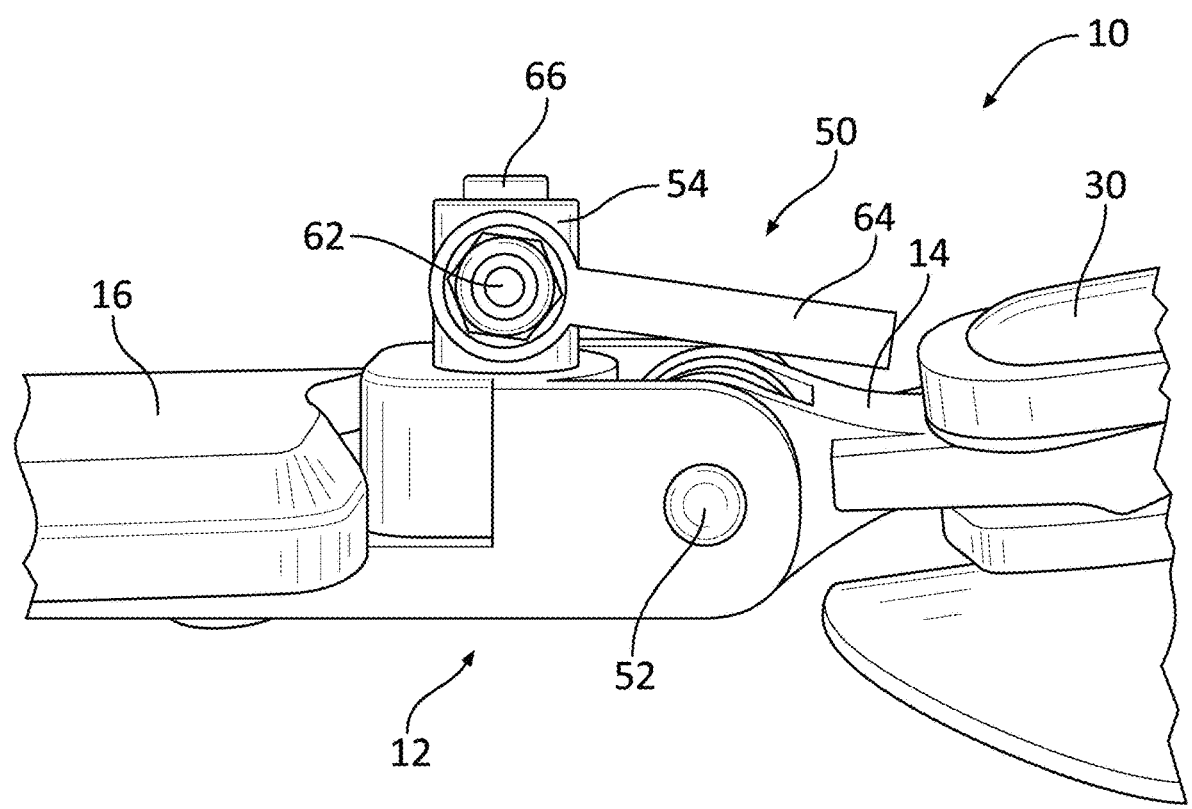
FIG. 28 is a detailed side perspective view of a joint for a knee brace apparatus with a tool fitting provided as a turn-key, according to some alternative embodiments of the present disclosure.
Figure 29:
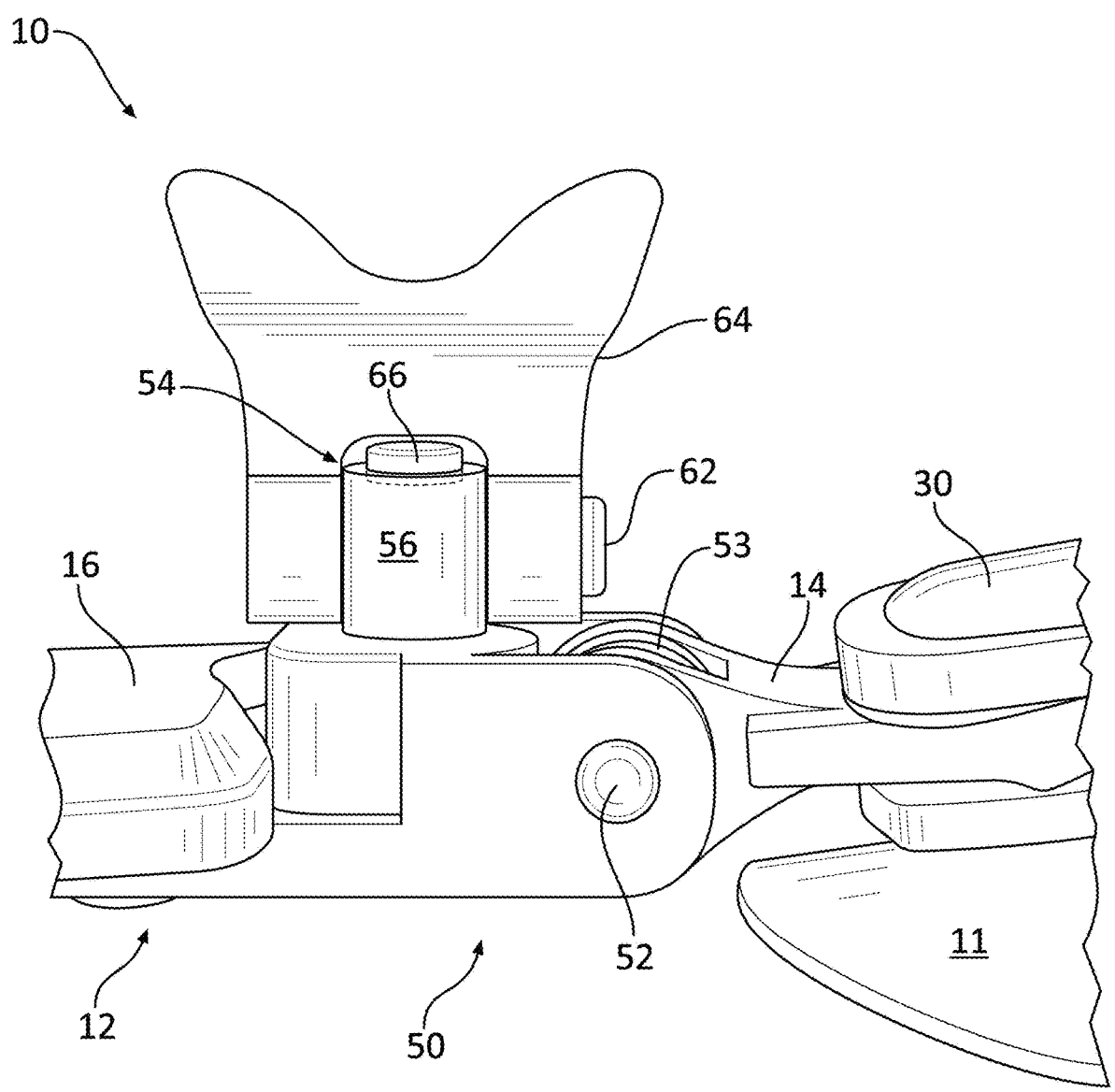
FIG. 29 is a detailed side perspective view of a joint for a knee brace apparatus with a tool fitting provided as a turn-key, according to some alternative embodiments of the present disclosure.

As a second example, and as depicted with reference to FIGS. 28-29, the first tool fitting 66 may be a first turn-key. For instance, the top surface of the distal portion 56 of the first pin 54 may include the first tool fitting 66 provided as a first turn-key (e.g., a nut) projecting off of the top surface of the distal portion 56 of the first pin 54. The first tool fitting 66, when provided as a first turn-key, may be configured to be grasped by a tool such as a wrench (e.g., open-ended wrench, socket wrench, etc.), which may be turned, thereby rotating the first pin 54 and operating the first joint 50 as discussed above. As depicted with reference to FIG. 6, the first manual adjustment tab 64 may be shaped to provide a gap 67 between the first manual adjustment tab 64 and the top surface of the distal portion 56 of the first pin 54. Accordingly, in such embodiments of the present disclosure where the first pin 54 includes the first tool fitting 66 provided as a first turn-key projecting from the first pin 54, the first manual adjustment tab 64 may still be pivoted about the first cross-bar 62 along the curvature 63 as depicted with reference to FIG. 11. For example, throughout the path of the first manual adjustment tab 64 along the curvature 63, the gap 67 may allow the first manual adjustment tab 64 to remain clear of the first tool fitting 66 provided as a first turn-key.

Figure 30:
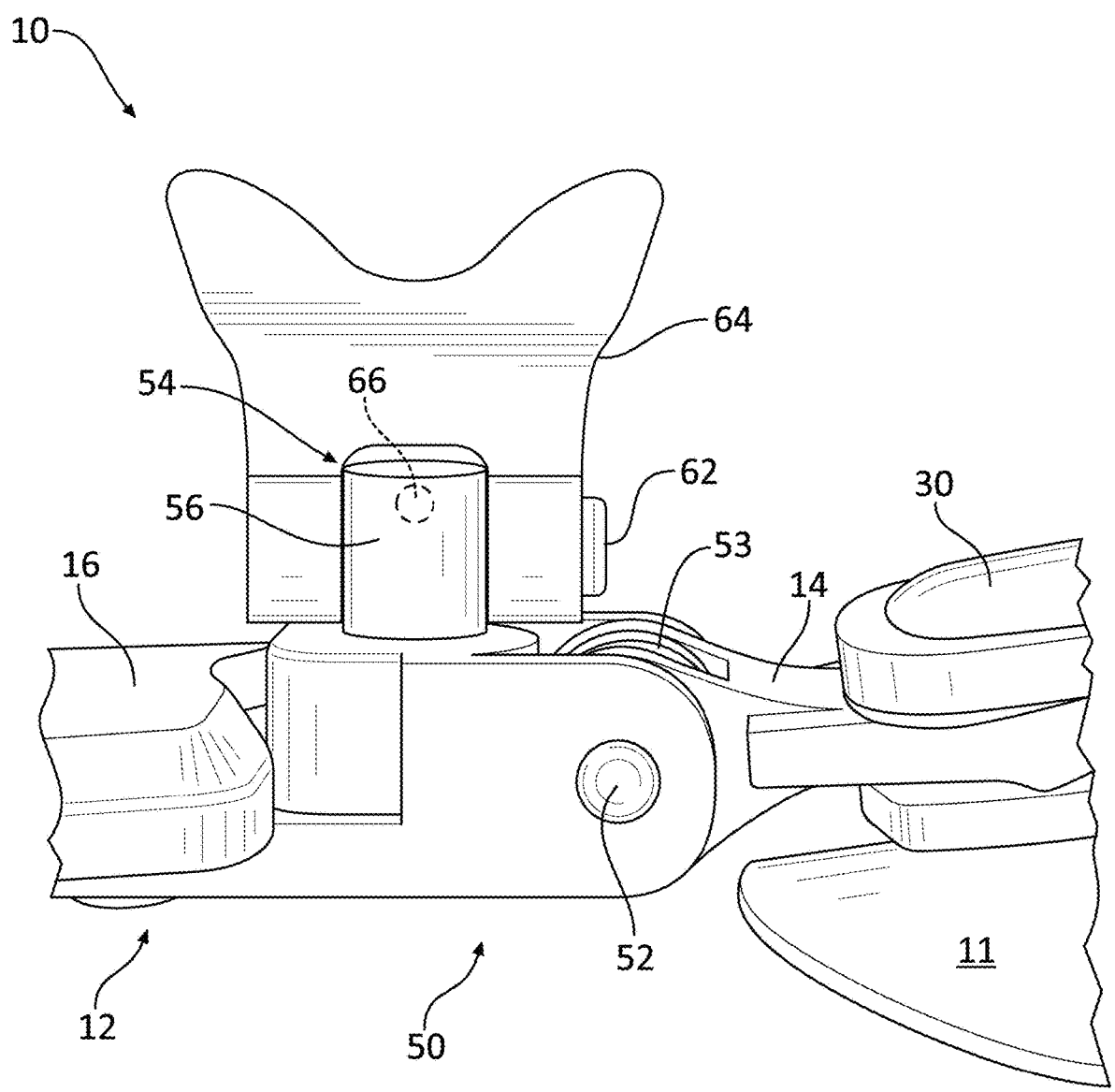
FIG. 30 is a detailed side perspective view of a joint for a knee brace apparatus with a tool fitting provided as a recess, according to some alternative embodiments of the present disclosure.

As a third example, and as depicted with reference to FIG. 30, the first tool fitting 66 may be a first recess (or a hole) extending through a side surface of the distal portion 56 of the first pin 56 (e.g., perpendicular to the central axis 59 of the first pin 54 depicted with reference to FIG. 6). In this sense, a tool may be inserted within the first tool fitting 66 provided as a first recess and turned, thereby rotating the first pin 54 and operating the first joint 50 as discussed above.

Advantageously, the user of the apparatus 10 (or the assembly 100, depending on the implementation) may thus be provided an option of turning the first pin 54 via the first manual adjustment tab 64, or turning the first pin 54 via a tool configured to engage the first tool fitting 66.

Figure 39:
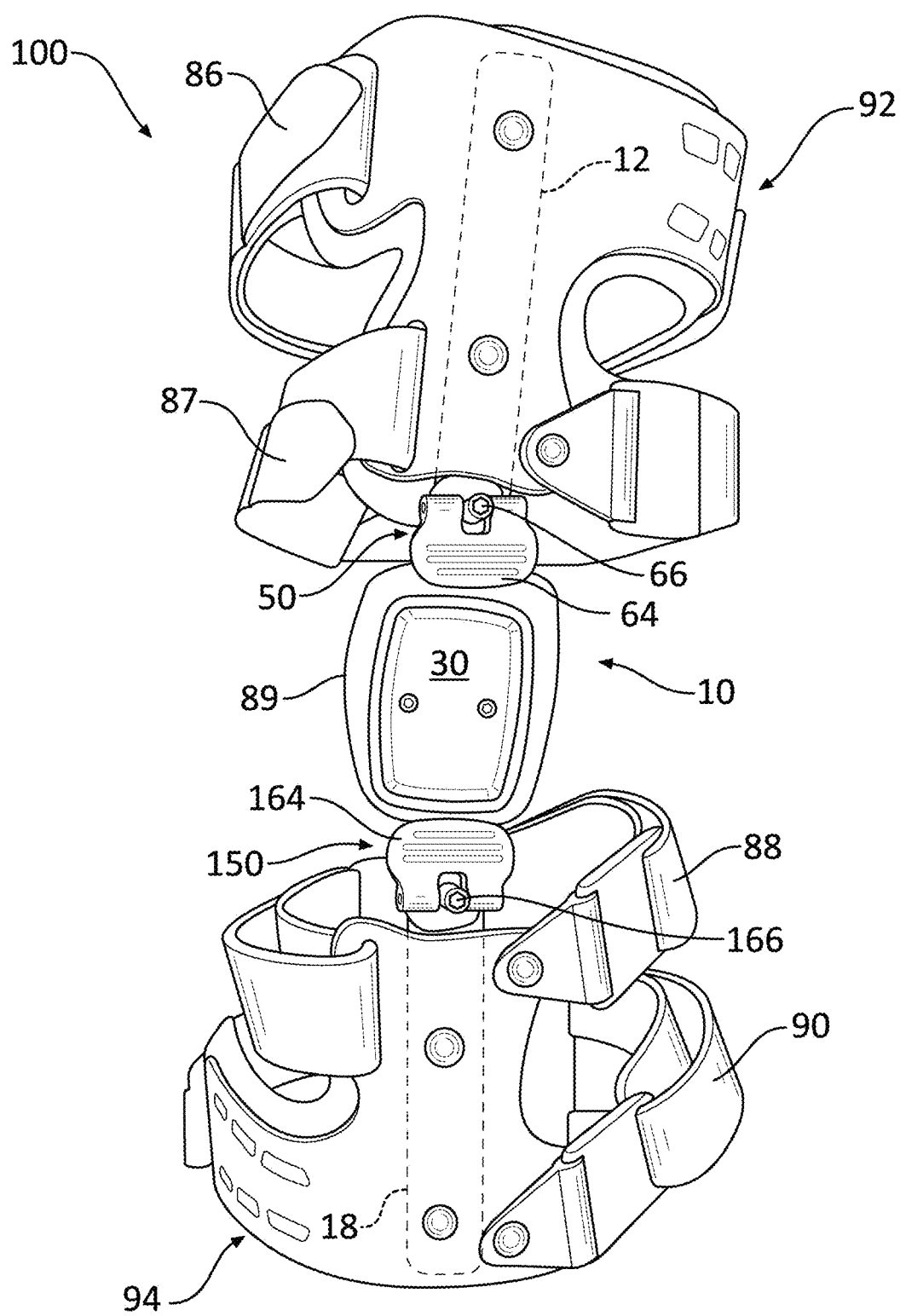
FIG. 39 is a side perspective view of a knee brace apparatus with two joints and two tool fittings, according to some alternative embodiments of the present disclosure.

Referring again to FIG. 25, the first tool fitting 66 on the first pin 54 may be analogously applied to the second pin mechanically engaged with the second joint 150, thereby providing a second tool fitting 166 (depicted with reference to FIG. 39) disposed on the second pin. Thus, in some embodiments, the second tool fitting 166 is a second key-hole extending into a top surface of a distal portion of the second pin. In other embodiments, the second tool fitting 166 is a second turn-key projecting off of a top surface of the distal portion of the second pin. In other embodiments still, the second tool fitting 166 is a second recess extending through a side surface of the distal portion of the second pin.

Figure 31:
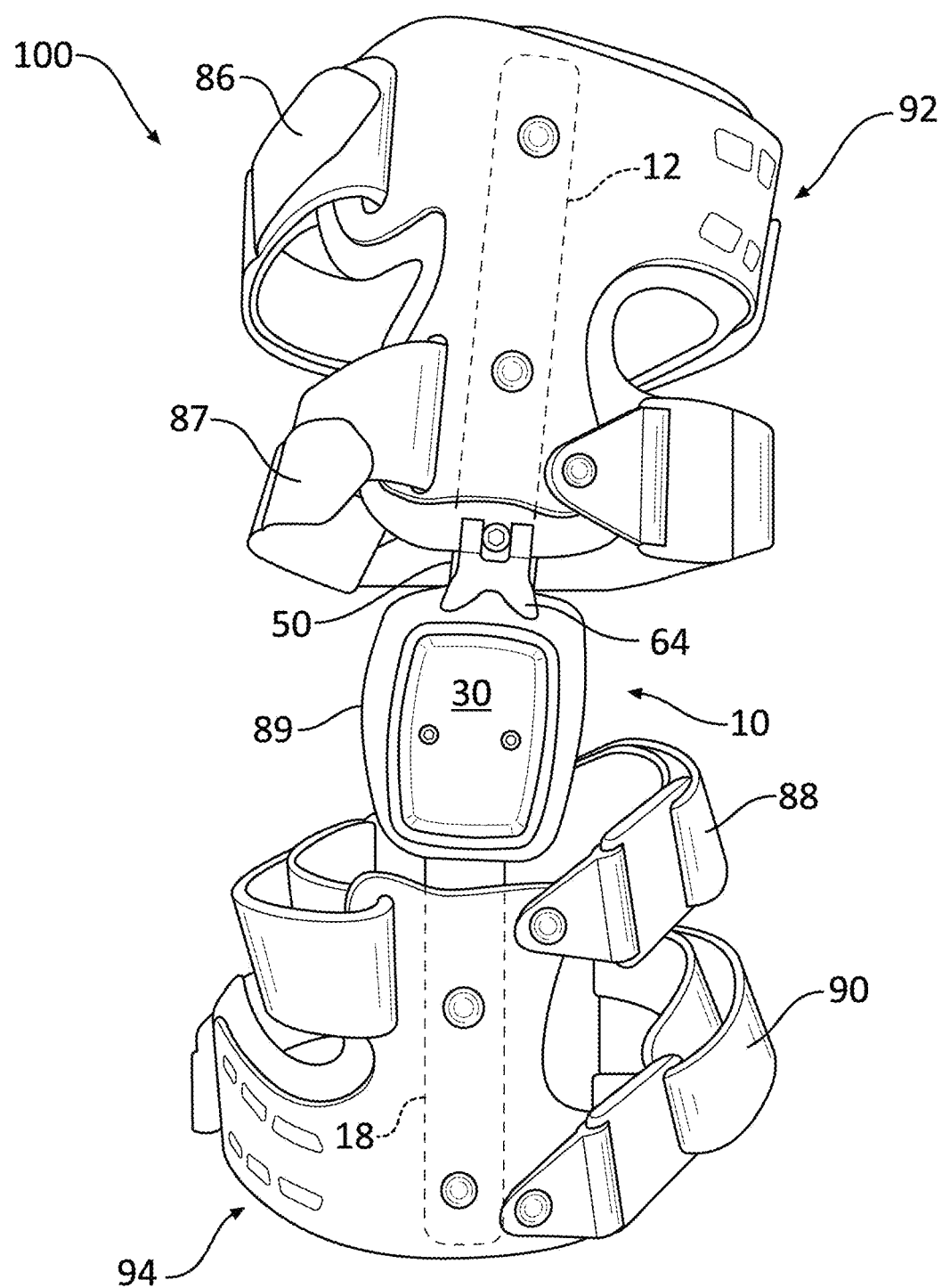
FIG. 31 is a side perspective view of a knee brace apparatus, according to some alternative embodiments of the present disclosure.
Figure 32:
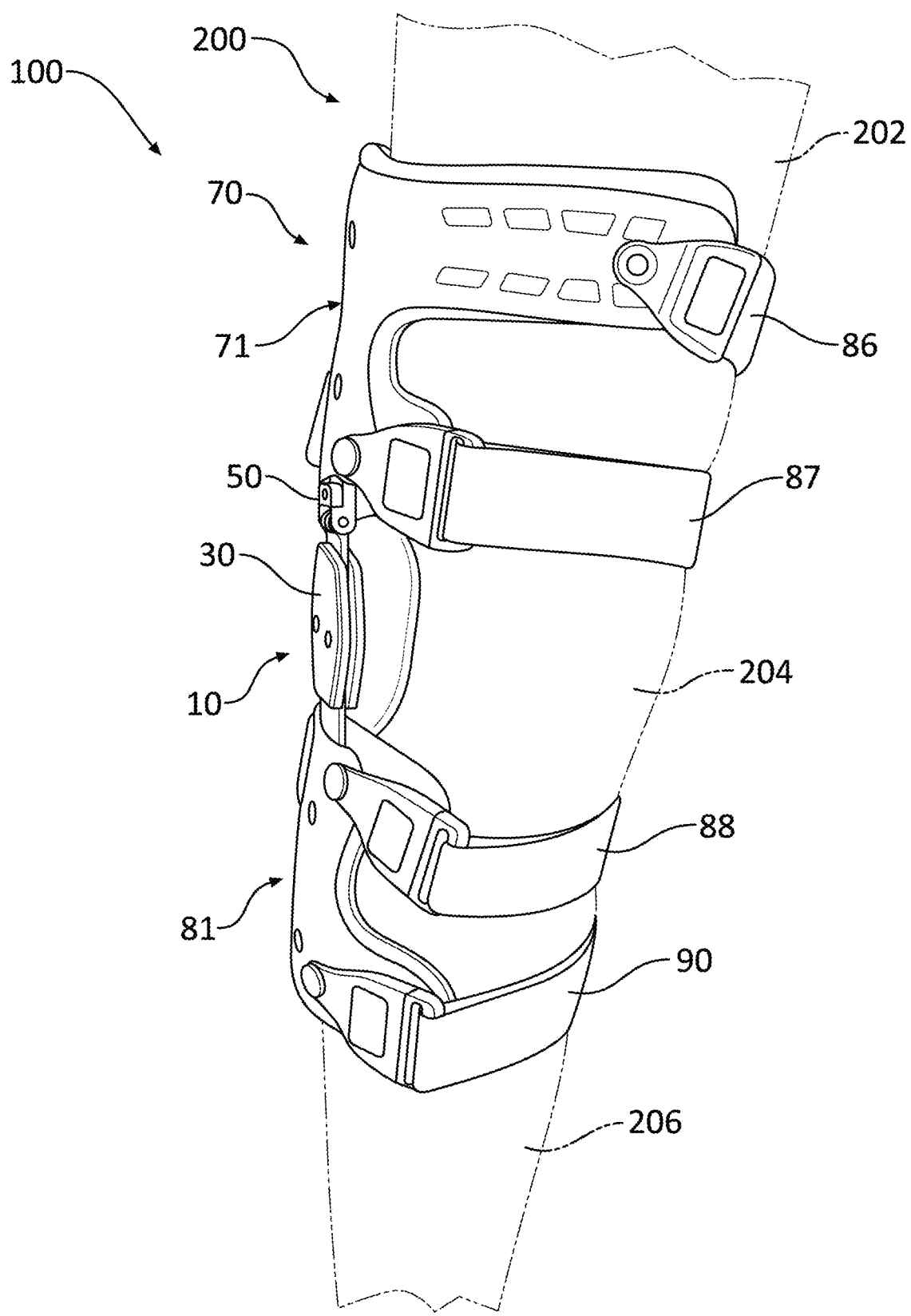
FIG. 32 is a front perspective view of a user wearing a knee brace apparatus, according to some alternative embodiments of the present disclosure.
Figure 33:
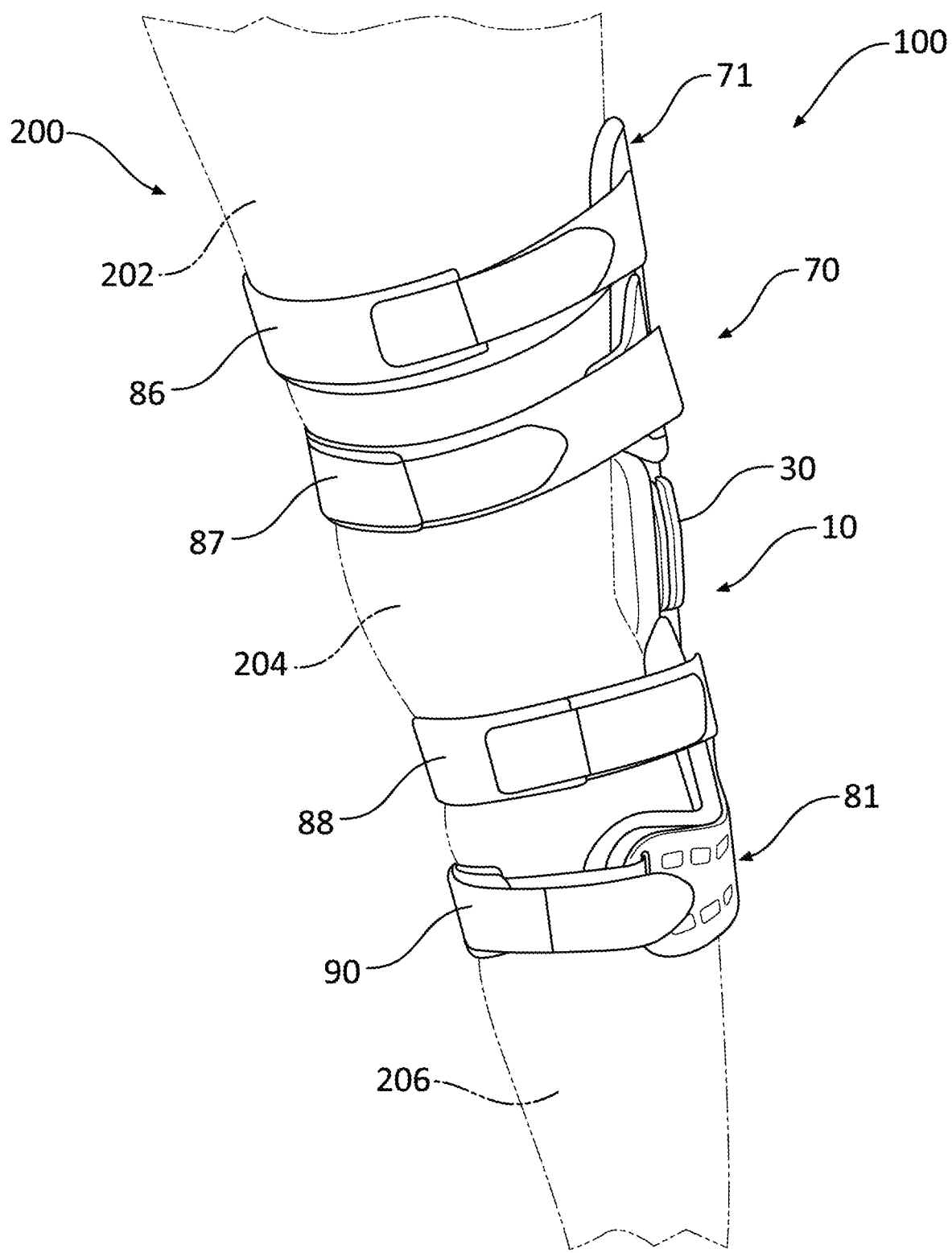
FIG. 33 is a rear perspective view of a user wearing a knee brace apparatus, according to some alternative embodiments of the present disclosure.
Figure 34:
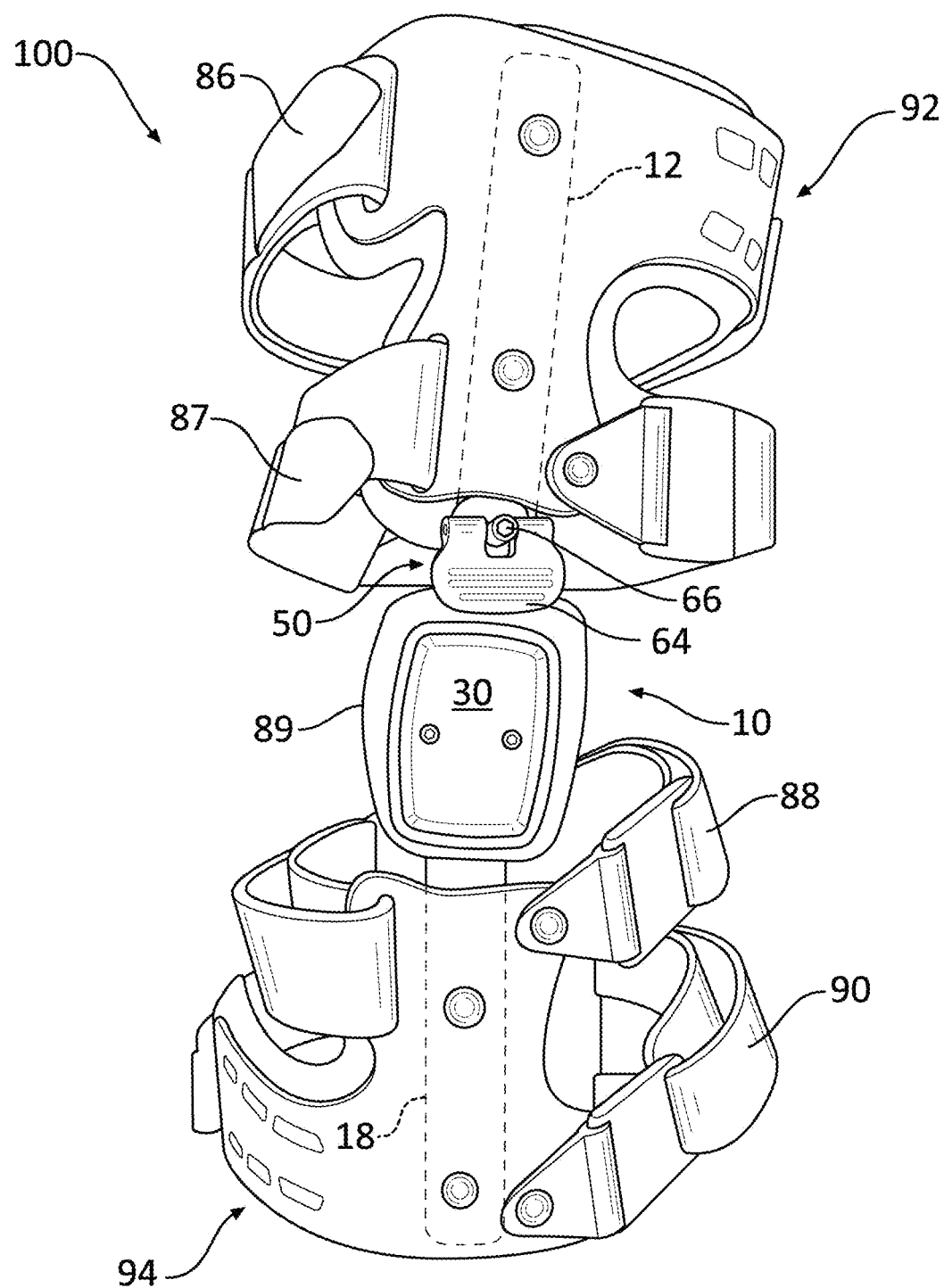
FIG. 34 is a side perspective view of a knee brace apparatus with a tool fitting, according to some alternative embodiments of the present disclosure.
Figure 35:
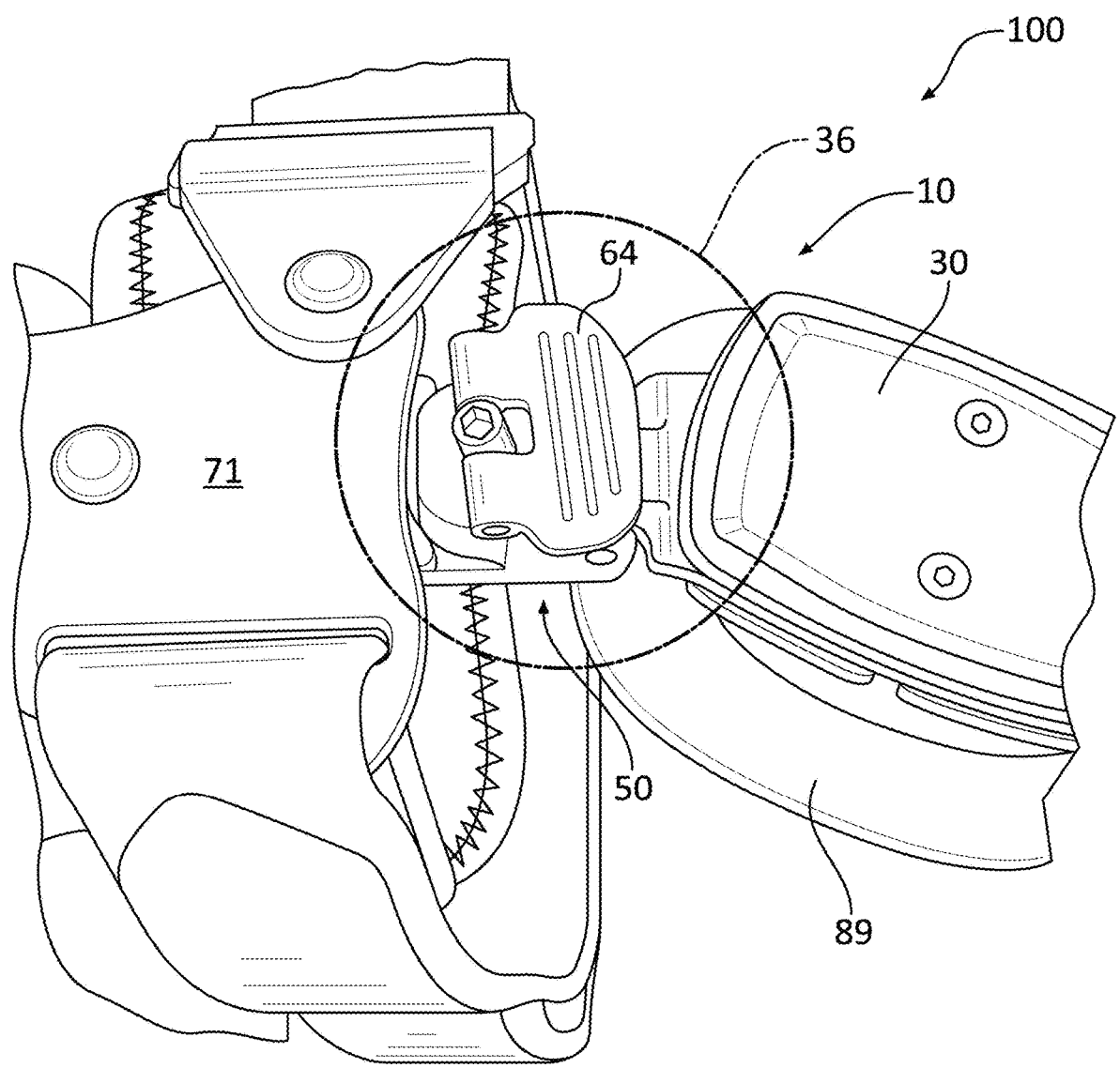
FIG. 35 is a side perspective view of a joint for knee brace apparatus with a tool fitting, according to some alternative embodiments of the present disclosure.
Figure 36:
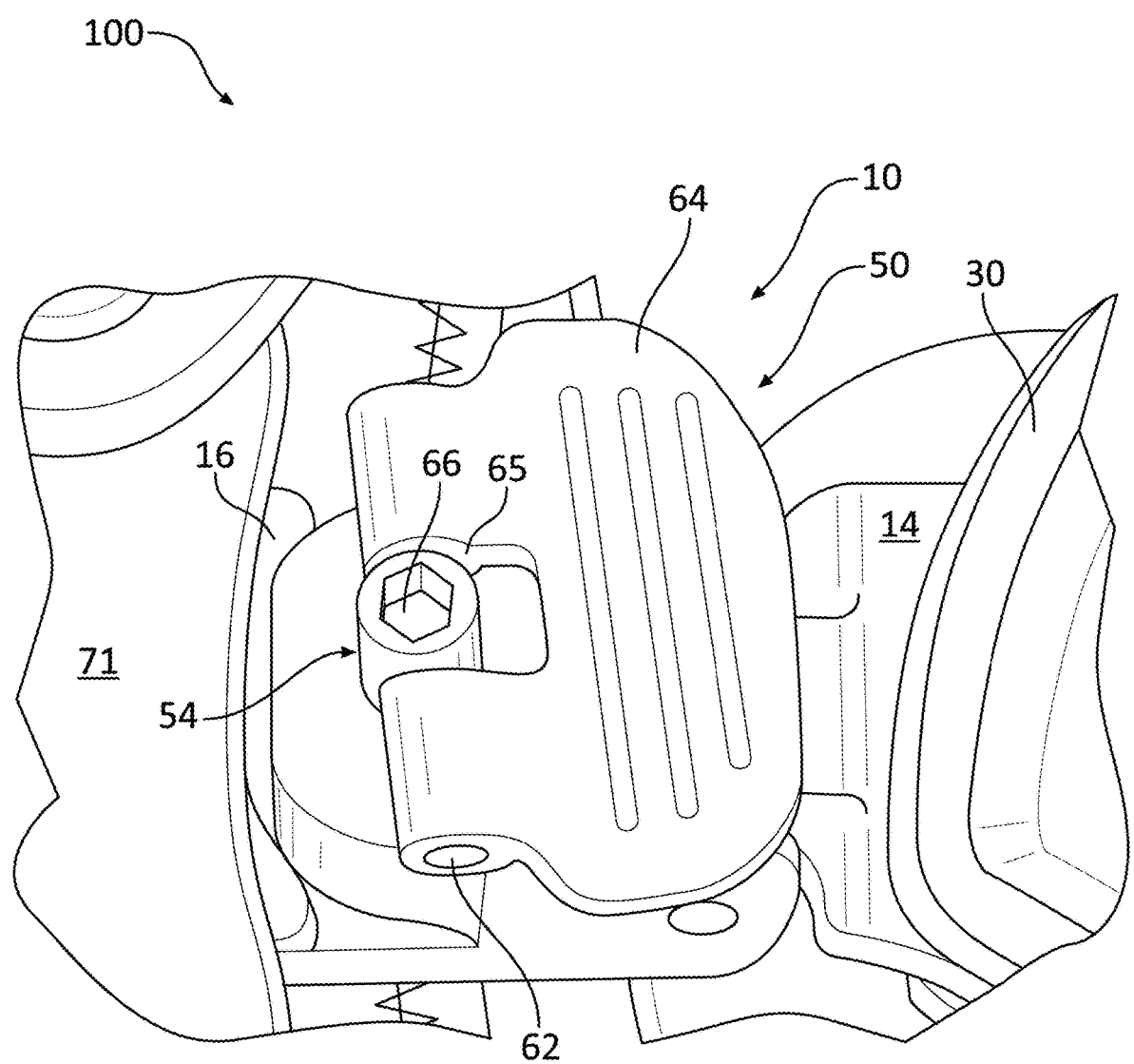
FIG. 36 is a detailed perspective view of a joint for a knee brace apparatus with a tool fitting, according to some alternative embodiments of the present disclosure.

Referring now to FIGS. 31-33, the assembly 100 is shown, according to some alternative embodiments of the present disclosure. For instance, the assembly 100 may be provided without the sleeve 70, while the apparatus 10 may be provided as discussed above (or substantially so). In this sense, the first cuff 71 (depicted with reference to FIG. 1) may be replaced with a thigh member 92, and the second cuff 81 (depicted with reference to FIG. 1) may be replaced with a calf member 94. The thigh and calf members 92, 94 may be configured as durable (e.g., plastic, nylon, etc.) panels formed to match the contours of the leg 200. In some embodiments, the first and second struts 12, 18 of the apparatus 10 are disposed on an interior surface of the thigh and calf members 92, 94. In other embodiments, the first and second struts 12, 18 are disposed within the material of the thigh and calf members 92, 94. In other embodiments still, the first and second struts 12, 18 and the thigh and calf members 92, 94 are formed as singular components (respectively). In such alternative embodiments, the thigh and calf members 92, 94 may be secured to the leg 200 via member straps 86, 87, 88, and 90 (rather than the first and second straps 74, 76, as well as the first, second, and third fasteners 78, 80, 82 depicted with reference to FIG. 16).

Referring now to FIGS. 34-38, the assembly 100 is shown with the first joint 50 including the first tool fitting 66, according to some alternative embodiments of the present disclosure. For instance, as discussed above with reference to FIGS. 26-30, the first tool fitting 66 may be provided on the first pin 54 as a key-hole, a turn-key, or a recess. As mentioned above with reference to FIGS. 26-27, the top surface of the distal portion 56 of the first pin 54 may include the first tool fitting 66 provided as a key-hole. As shown via the exemplary embodiment depicted with reference to FIG. 34, the first tool fitting 66 is provided as a key-hole. However, in other such alternative embodiments, the first tool fitting 66 may be provided as a turn-key or a recess as discussed above with reference to FIGS. 28-30. Thus, the first joint 50 may be operated via manual articulation of the first manual adjustment tab 64 (as depicted with reference to FIG. 37), or alternatively operated via use of a tool such as the Allen wrench 99 (as depicted with reference to FIG. 38).

In some embodiments, and as depicted with reference to FIGS. 1, 6, 9, 12, 13, 15, and 31, the first manual adjustment tab is formed in a "butterfly" shape. However, it should be appreciated that the first manual adjustment tab 64 may be formed in any suitable shape. For example, as depicted with reference to FIGS. 34-38, the first manual adjustment tab 64 may be formed in a semi-circular shape. In some embodiments, and as suggested via the depictions with reference to FIGS. 1, 6, 9, 12, 13, 15, and 31, the first manual adjustment tab 64 may be made of plastic, and may be provided in a clear (e.g., see-through) configuration. However, it should be appreciated that the first manual adjustment tab 64 may be constructed of any suitable material. For example, as depicted with reference to FIGS. 34-38, the first manual adjustment tab may be constructed of steel or some other heavier material.

As mentioned above with reference to FIG. 25, the first tool fitting 66 on the first pin 54 may be analogously applied to the second pin mechanically engaged with the second joint 150, thereby providing the second tool fitting 166 disposed on the second pin. Thus, it should be appreciated that the alternative embodiments discussed with reference to FIGS. 26-38 may be applied analogously to the alternative embodiments of the assembly 100 that include the second joint 150 (as depicted with reference to FIG. 25). Accordingly, the various alternative embodiments of the first joint 50 depicted with reference to FIGS. 33-38 may be equivalently applied to the second joint 150. For example, and referring now to FIG. 39, the assembly 100 is shown to include the first joint 50 including the first (e.g., upper) tool fitting 66, as well as the second joint 150 including the second (e.g., lower) tool fitting 166, according to some embodiments of the present disclosure. The second tool fitting 166 may be configured similar to the first tool fitting 66, and therefore the second tool fitting 166 may be provided as the second key-hole extending into a top surface of the distal portion of the second pin, the second turn-key projecting off of a top surface of the distal portion of the second pin, or the second recess extending through the side surface of the distal portion of the second pin, as discussed above with reference to FIGS. 26-30.

Thus, although there have been described particular embodiments of the present invention of a new and useful KNEE BRACE APPARATUS it is not intended that such references be construed as limitations upon the scope of this invention.

What is claimed is:

1. A knee brace apparatus, comprising:
   a hinge;
   a first strut including a proximal portion disposed on the hinge, a distal portion configured to be secured above a knee of a leg, and a first joint connecting the proximal portion of the first strut to the distal portion of the first strut, such that the distal portion of the first strut is configured to pivot about a first anteroposterior axis defined by the first joint, wherein the first strut is configured to pivot about a first mediolateral axis with respect to the hinge;

a second strut including a proximal portion disposed on the hinge and a distal portion configured to be secured below the knee of the leg, wherein the second strut is configured to pivot about a second mediolateral axis with respect to the hinge;

a first pin disposed on the distal portion of the first strut and mechanically engaged with the first joint, wherein the first pin is configured to be rotated relative to the first joint;

a first cross-bar disposed on the first pin;

a first manual adjustment tab disposed on the first cross-bar, wherein the first manual adjustment tab is configured to be pivoted about the first cross-bar and rotated relative to the first joint; and a first tool fitting disposed on the first pin, wherein when the first manual adjustment tab is rotated relative to the first joint, the first pin is rotated relative to the first joint, such that the mechanical engagement between the first pin and the first joint effectuates pivoting the distal portion of the first strut about the first anteroposterior axis.

2. The apparatus of claim 1, wherein the first pin includes a proximal portion mechanically engaged with the first joint and a distal portion extending free of the first joint, wherein the proximal portion of the first pin includes a first set of threading, and wherein the first joint includes a first set of teeth mechanically engaged with the first set of threading on the proximal portion of the first pin, such that when the first pin is rotated relative to the first joint, the first pin is pivoted relative to the first joint, and the distal portion of the first strut is pivoted about the first anteroposterior axis.

3. The apparatus of claim 2, wherein the second strut further includes a second joint connecting the proximal portion of the second strut to the distal portion of the second strut, such that the distal portion of the second strut is configured to pivot about a second anteroposterior axis defined by the second joint, wherein the apparatus further comprises:
    a second pin disposed on the distal portion of the second strut and mechanically engaged with the second joint, wherein the second pin is configured to be rotated relative to the second joint;
    a second cross-bar disposed on the second pin; and
    a second manual adjustment tab disposed on the second cross-bar, wherein the second manual adjustment tab is configured to be pivoted about the second cross-bar and rotated relative to the second joint; and
    a second tool fitting disposed on the second pin, wherein when the second manual adjustment tab is rotated relative to the second joint, the second pin is rotated relative to the second joint, such that the mechanical engagement between the second pin and the second joint effectuates pivoting the distal portion of the second strut about the second anteroposterior axis.

4. The apparatus of claim 3, wherein the second pin includes a proximal portion mechanically engaged with the second joint and a distal portion free of the second joint, wherein the proximal portion of the second pin includes a second set of threading, and wherein the second joint includes a second set of teeth mechanically engaged with the second set of threading on the proximal portion of the second pin, such that when the second pin is rotated relative to the second joint, the second pin is pivoted relative to the second joint, and the distal portion of the second strut is pivoted about the second anteroposterior axis.

5. The apparatus of claim 2, wherein the first tool fitting is a first key-hole extending into a top surface of the distal portion of the first pin.

6. The apparatus of claim 2, wherein the first tool fitting is a first turn-key projecting off of a top surface of the distal portion of the first pin.

7. The apparatus of claim 4, wherein the first tool fitting is a first key-hole extending into a top surface of the distal portion of the first pin, and wherein the second tool fitting is a second key-hole extending into a top surface of the distal portion of the second pin.

8. The apparatus of claim 4, wherein the first tool fitting is a first turn-key projecting off of a top surface of the distal portion of the first pin, and wherein the second tool fitting is a second turn-key projecting off of a top surface of the distal portion of the second pin.

9. A knee brace apparatus, comprising:

a hinge;

a first strut including a proximal portion disposed on the hinge, a distal portion configured to be secured above a knee of a leg, and a first joint connecting the proximal portion of the first strut to the distal portion of the first strut, such that the distal portion of the first strut is configured to pivot about a first anteroposterior axis defined by the first joint, wherein the first strut is configured to pivot about a first mediolateral axis with respect to the hinge;

a second strut including a proximal portion disposed on the hinge, a distal portion configured to be secured below the knee of the leg, and a second joint connecting the proximal portion of the second strut to the distal portion of the second strut, such that the distal portion of the second strut is configured to pivot about a second anteroposterior axis defined by the second joint, wherein the second strut is configured to pivot about a second mediolateral axis with respect to the hinge;

a first pin disposed on the distal portion of the first strut and mechanically engaged with the first joint, wherein the first pin is configured to be rotated relative to the first joint;

a second pin disposed on the distal portion of the second strut and mechanically engaged with the second joint, wherein the second pin is configured to be rotated relative to the second joint;

a first cross-bar disposed on the first pin;

a second cross-bar disposed on the second pin;

a first manual adjustment tab disposed on the first cross-bar, wherein the first manual adjustment tab is configured to be pivoted about the first cross-bar and rotated relative to the first joint; and a second manual adjustment tab disposed on the second cross-bar, wherein the second manual adjustment tab is configured to be pivoted about the second cross-bar and rotated relative to the second joint, wherein when the first manual adjustment tab is rotated relative to the first joint, the first pin is rotated relative to the first joint, such that the mechanical engagement between the first pin and the first joint effectuates pivoting the distal portion of the first strut about the first anteroposterior axis, and wherein when the second manual adjustment tab is rotated relative to the second joint, the second pin is rotated relative to the second joint, such that the mechanical engagement between the second pin and the second joint effectuates pivoting the distal portion of the second strut about the second anteroposterior axis.

10. The apparatus of claim 9, wherein the first pin includes a proximal portion mechanically engaged with the first joint and a distal portion extending free of the first joint,
wherein the proximal portion of the first pin includes a first set of threading,
wherein the first joint includes a first set of teeth mechanically engaged with the first set of threading on the proximal portion of the first pin, such that when the first pin is rotated relative to the first joint, the first pin is pivoted relative to the first joint, and the distal portion of the first strut is pivoted about the first anteroposterior axis,
wherein the second pin includes a proximal portion mechanically engaged with the second joint and a distal portion free of the second joint,
wherein the proximal portion of the second pin includes a second set of threading, and
wherein the second joint includes a second set of teeth mechanically engaged with the second set of threading on the proximal portion of the second pin, such that when the second pin is rotated relative to the second joint, the second pin is pivoted relative to the second joint, and the distal portion of the second strut is pivoted about the second anteroposterior axis.

11. The apparatus of claim 10, further comprising a first tool fitting disposed on the first pin.

12. The apparatus of claim 11, further comprising a second tool fitting disposed on the second pin.

13. The apparatus of claim 12, wherein the first tool fitting is a first key-hole extending into a top surface of the distal portion of the first pin, and
wherein the second tool fitting is a second key-hole extending into a top surface of the distal portion of the second pin.

14. The apparatus of claim 12, wherein the first tool fitting is a first turn-key projecting off of a top surface of the distal portion of the first pin, and
wherein the second tool fitting is a second turn-key projecting off of a top surface of the distal portion of the second pin.

15. The apparatus of claim 12, wherein the first tool fitting is a first recess extending into a side surface of the distal portion of first pin, and
wherein the second tool fitting is a second recess extending into a side surface of the distal portion of the second pin.

16. A knee brace method, comprising:
providing a hinge;
providing a first strut including a proximal portion disposed on the hinge, a distal portion, and a first joint connecting the proximal portion of the first strut to the distal portion of the first strut;
providing a second strut including a proximal portion disposed on the hinge and a distal portion disposed on the second cuff;
providing a first pin disposed on the distal portion of the first strut and mechanically engaged with the first joint;
providing a first cross-bar disposed on the first pin;
providing a first manual adjustment tab disposed on the first cross-bar;
providing a first tool fitting disposed on the first pin;
securing the distal portion of the first strut to a thigh of a leg;
securing the distal portion of the second strut to a calf of a leg;
pivoting the first strut about a first mediolateral axis with respect to the hinge;
pivoting the second strut about a second mediolateral axis with respect to the hinge;
pivoting the first manual adjustment tab about the first cross-bar;
rotating the first manual adjustment tab, such that the first pin is rotated relative to the first joint, and the mechanical engagement between the first pin and the first joint effectuates pivoting the distal portion of the first strut about a first anteroposterior axis; and
engaging the first tool fitting with a tool, such that the first pin is rotated relative to the first joint, and the mechanical engagement between the first pin and the first joint effectuates pivoting the distal portion of the first strut about the first anteroposterior axis.

17. The method of claim 16, wherein the second strut further includes a second joint connecting the proximal portion of the second strut to the distal portion of the second strut, and
wherein the method further comprises:
providing a second pin disposed on the distal portion of the second strut and mechanically engaged with the second joint;
providing a second cross-bar disposed on the second pin;
providing a second manual adjustment tab disposed on the second cross-bar;
providing a second tool fitting disposed on the second pin;
pivoting the second manual adjustment tab about the second cross-bar;
rotating the second manual adjustment tab, such that the second pin is rotated relative to the second joint, and the mechanical engagement between the second pin and the second joint effectuates pivoting the distal portion of the second strut about a second anteroposterior axis; and
engaging the second tool fitting with the tool, such that the second pin is rotated relative to the second joint, and the mechanical engagement between the second pin and the second joint effectuates pivoting the distal portion of the second strut about the second anteroposterior axis.

18. The method of claim 17, wherein the first pin includes a proximal portion mechanically engaged with the first joint and a distal portion extending free of the first joint,
wherein the second pin includes a proximal portion mechanically engaged with the second joint and a distal portion extending free of the second joint,
wherein the first tool fitting is a first key-hole extending into a top surface of the distal portion of the first pin, and
wherein the second tool fitting is a second key-hole extending into a top surface of the distal portion of the second pin.

19. The method of claim 17, wherein the first pin includes a proximal portion mechanically engaged with the first joint and a distal portion extending free of the first joint,
wherein the second pin includes a proximal portion mechanically engaged with the second joint and a distal portion extending free of the second joint, wherein the first tool fitting is a first turn-key projecting off of a top surface of the distal portion of the first pin, and wherein the second tool fitting is a second turn-key projecting off of a top surface of the distal portion of the second pin.

20. The method of claim 17, wherein the first pin includes a proximal portion mechanically engaged with the first joint and a distal portion extending free of the first joint, wherein the second pin includes a proximal portion mechanically engaged with the second joint and a distal portion extending free of the second joint, wherein the first tool fitting is a first recess extending into a side surface of the distal portion of first pin, and wherein the second tool fitting is a second recess extending into a side surface of the distal portion of the second pin.

* * * * *